US010413597B2

(12) United States Patent
Quinn et al.

(10) Patent No.: US 10,413,597 B2
(45) Date of Patent: Sep. 17, 2019

(54) METHODS OF TREATING MUCOPOLYSACCHARIDOSIS IIIB (MPSIIIB)

(71) Applicant: ALEXION PHARMACEUTICALS, INC., New Haven, CT (US)

(72) Inventors: Anthony Quinn, Gloucester, MA (US); Sandra Rojas-Caro, Waltham, MA (US); Anthony Rossomando, Cambridge, MA (US); Robert John Lyng, Lexington, MA (US); Kim Lynette Askew, Lincoln, MA (US); Nelson Hsia, Cambridge, MA (US); Kiran Patki, Lexington, MA (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 41 days.

(21) Appl. No.: 15/514,962

(22) PCT Filed: Sep. 29, 2015

(86) PCT No.: PCT/US2015/052921
§ 371 (c)(1),
(2) Date: Mar. 28, 2017

(87) PCT Pub. No.: WO2016/054025
PCT Pub. Date: Apr. 7, 2016

(65) Prior Publication Data
US 2017/0216413 A1 Aug. 3, 2017

Related U.S. Application Data

(60) Provisional application No. 62/057,030, filed on Sep. 29, 2014.

(51) Int. Cl.
| *C12P 7/48* | (2006.01) |
| *A61K 38/47* | (2006.01) |
| *A61K 38/38* | (2006.01) |
| *C12N 9/24* | (2006.01) |

(52) U.S. Cl.
CPC .............. *A61K 38/47* (2013.01); *A61K 38/38* (2013.01); *C12N 9/2402* (2013.01); *C12Y 302/0105* (2013.01)

(58) Field of Classification Search
None
See application file for complete search history.

(56) References Cited

U.S. PATENT DOCUMENTS

| 5,362,852 | A | 11/1994 | Geoghegan |
| 5,897,998 | A | 4/1999 | Speksnijder et al. |
| 6,670,165 | B2 | 12/2003 | Canfield |
| 6,730,822 | B1 | 5/2004 | Ivarie et al. |
| 6,825,396 | B2 | 11/2004 | MacArthur |
| 6,875,588 | B2 | 4/2005 | Harvey et al. |
| 7,138,262 | B1 | 11/2006 | Daniel |
| 7,294,507 | B2 | 11/2007 | Harvey et al. |
| 7,521,591 | B2 | 4/2009 | Ivarie et al. |
| 7,534,929 | B2 | 5/2009 | Ivarie et al. |
| 9,012,168 | B2 | 4/2015 | Ruiz et al. |
| 2006/0185024 | A1 | 8/2006 | Ivarie et al. |
| 2007/0243165 | A1 | 10/2007 | Ivarie et al. |
| 2008/0064862 | A1 | 3/2008 | Harvey et al. |
| 2009/0022702 | A1 | 1/2009 | Zhu |
| 2009/0253176 | A1 | 10/2009 | Parker et al. |
| 2011/0318327 | A1 | 12/2011 | Concino et al. |
| 2012/0003202 | A1 | 1/2012 | Calias et al. |
| 2013/0095092 | A1 | 4/2013 | Quinn et al. |
| 2013/0121984 | A1 | 5/2013 | Haslett et al. |
| 2013/0189718 | A1 | 7/2013 | Ruiz et al. |
| 2014/0255383 | A1 | 9/2014 | Quinn et al. |
| 2018/0105879 | A1 | 4/2018 | Ji et al. |

FOREIGN PATENT DOCUMENTS

| WO | WO 94/12650 A2 | 6/1994 |
| WO | WO 01/68882 A2 | 9/2001 |
| WO | WO 2007/070488 A2 | 6/2007 |
| WO | WO 2011/163652 A2 | 12/2011 |
| WO | WO 2013/055888 A2 | 4/2013 |
| WO | WO 2016/054025 A1 | 4/2016 |
| WO | WO 2017/132675 A1 | 8/2017 |

OTHER PUBLICATIONS

Fu et al. (The Am. Society of Gene & Cell Therapy 9bol. 19, No. 6, pp. 1025-1033).*
Gaffke et al., (Metab. Brain Dis., 2018, vol. 33, pp. 1-10).*
International Patent Application No. PCT/US2015/052921, filed Sep. 29, 2015; International Preliminary Report on Patentability dated Apr. 13, 2017; 9 pages.
International Patent Application No. PCT/US2015/052921, filed Sep. 29, 2015; International Search Report and Written Opinion dated Jan. 14, 2016; 11 pages.
Adames et al., "The c-myc oncogene driven by immunoglobulin enhancers induces lymphoid malignancy in transgenic mice" Nature, Dec. 12-18, 1985; 318(6046):533-8.
Alexander et al., "Expression of the c-myc oncogene under control of an immunoglobulin enhancer in E mu-myc transgenic mice" Mol Cell Biol, Apr. 1987; 7(4):1436-44.
Altschul et al., "Basic Local Alignment Search Tool" J Mol Biol, Oct. 5, 1990; 215(3):403-10.
Altschul et al., "Gapped BLAST and PSI-BLAST: a new generation of protein database search programs" Nucleic Acids Research, Sep. 1, 1997; 25(17):3389-402.
Ausubel et al., *Current Protocols in Immunology*, John Wiley & Sons, New York, N.Y.; 1987. Cover page, title page and table of contents.
Ausubel et al., *Current Protocols in Molecular Biology*, John Wiley & Sons, New York, N.Y.; 1989. Cover page, title page and table of contents.

(Continued)

*Primary Examiner* — Hope A Robinson
(74) *Attorney, Agent, or Firm* — Mueting, Raasch & Gebhardt, P.A.

(57) ABSTRACT

Methods for treating the central nervous system (CNS) in a human patient with mucopolysaccharidosis (MPS) MB who has an intact blood brain barrier, comprising intravenous administration of recombinant NaGlu.

10 Claims, 14 Drawing Sheets

Specification includes a Sequence Listing.

(56) References Cited

OTHER PUBLICATIONS

Beniaminovitz et al., "Prevention of rejection in cardiac transplantation by blockade of the interleukin-2 receptor with a monoclonal antibody" New Engl J Med, Mar. 2, 2000; 324(9):613-9.
Benoist et al., "In vivo sequence requirements of the SV40 early promotor region" Nature, Mar. 26, 1981; 290(5804):304-10.
Berard et al., "A Review of Interleukin-2 Receptor Antagonists in Solid Organ Transplantation" Pharmacotherapy, Oct. 1999; 19(10):1127-37.
Bergamino et al., "Measurement of Blood-Brain Barrier Permeability with T1-Weighted Dynamic Contrast-Enhanced MRI in Brain Tumors: A Comparative Study with Two Different Algorithms" ISRN Neuroscience, Feb. 20, 2013; 2013, Article ID 905279, 6 pages. [online] [retrieved on Dec. 6, 2017]. Retrieved from <http://dx.doi.org/10.1155/2013/905279>.
Bickel, "How to measure drug transport across the blood-brain barrier" NeuroRx, Jan. 2005; 2(1):15-26.
Birren et al., Genome Analysis: A Laboratory Manual, Cold Spring Harbor Laboratory Press, Harbor, NY; 1998. Cover page, title page, and table of contents.
Boje, "In vivo measurement of blood-brain barrier permeability" Current Protocols in Neuroscience, Aug. 2001; Ch 7: Unit 7.19.
Bowman et al., "Blood-brain barrier impairment in Alzheimer disease: stability and functional significance" Neurology, May 22, 2007; 68(21):1809-14.
Branco et al., "Selective deletion of antigen-specific, activated T cells by a humanized MAB to CD2 (MEDI-507) is mediated by NK cells" Transplantation, Nov. 27, 1999; 68(10):1588-96.
Brinster et al., "Regulation of metallothionein—thymidine kinase fusion plasmids injected into mouse eggs" Nature, Mar. 4, 1982; 296(5852):39-42.
Buckley, "Uncertainty in the analysis of tracer kinetics using dynamic contrast-enhanced T1-weighted MRI" Magn Reson Med, Mar. 2002; 47(3):601-6.
Chirmule et al., "Readministration of adenovirus vector in nonhuman primate lungs by blockade of CD40-CD40 ligand interactions" J Virol, Apr. 2000; 74(7):3345-52.
Chow et al., "4-Methylumbelliferyl 2-acetamido-2-deoxy-alpha-D-glucopyranoside, a fluorogenic substrate for N-acetyl-alpha-D-glucosaminidase" Carbohydrate Research, Oct. 1, 1981; 96(1):87-93.
Christenson et al., "Interpretation of cerebrospinal fluid protein assays in various neurologic diseases" Clin Chem, Jun. 1983; 29(6):1028-30.
Cosset et al., "Improvement of avian leukosis virus (ALV)-based retrovirus vectors by using different cis-acting sequences from ALVs" J Virol, Jun. 1991; 65(6):3388-94.
DeBoer et al., "The tac promoter: a functional hybrid derived from the trp and lac promoters" Proc. Natl. Acad. Sci. U.S.A. Jan. 1983; 80:21-5.
Dekaban, "Changes in brain weights during the span of human life: relation of brain weights to body heights and body weights" Ann Neural, Oct. 1978; 4(4):345-56.
Eckhoff et al., "The safety and efficacy of a two-dose daclizumab (zenapax) induction therapy in liver transplant recipients" Transplantation, May 15, 2000; 69(9):1867-72.
Eckstein, Oligonucleotides and Analogues: A Practical Approach, IRL Press, Ithaca, NY; 1991. Cover page, title page and table of contents.
Eeg-Olofsson et al., "Concentrations of CSF proteins as a measure of blood brain barrier function and synthesis of IgG within the CNS in 'normal' subjects from the age of 6 months to 30 years" Acta Paediatr Scand, Mar. 1981; 70(2):167-70.
Ekberg et al., "Daclizumab prevents acute rejection and improves patient survival post transplantation: 1 year pooled analysis" Transpl Int, 2000; 13(2):151-9.

Eyal-Giladi and Kochav, "From cleavage to primitive streak formation: a complementary normal table and a new look at the first stages of the development of the chick. I. General morphology" Dev Biol, Apr. 1976; 49(2):321-37.
Fishwild et al., "Differential Effects of Administration of a Human Anti-CD4 Monoclonal Antibody, HM6G, in Nonhuman Primates" Clin Immunol, Aug. 1999; 92(2):138-52.
Frolich et al., "Integrity of the blood-CSF barrier in dementia of Alzheimer type: CSF/serum rations of albumin and IgG" Eur Arch Psychiatry Clin Neurosci, 1991; 240:363-6.
Gait, Oligonucleotide Synthesis: A Practical Approach, Oxford University Press, Oxford, England, UK; 1984. Cover page, title page and table of contents.
Garbuzova-Davis et al., "Blood-brain barrier impairment in an animal model of MPS III B" PLoS One, Mar. 7, 2011; 6(3):e16601.
Garbuzova-Davis et al., "Blood-brain barrier impairment in MPS III patients" BMC Neurol., Nov. 13, 2013; 13:174.
Gardner et al., "The complete nucleotide sequence of an infectious clone of cauliflower mosaic virus by M13mp7 shotgun sequencing" Nucl. Acids Res, Jun. 25, 1981; 9(12):2871-88.
Gaziev et al., "Chronic graft-versus-host disease: is there an alternative to the conventional treatment?" Bone Marrow Transplant, Apr. 2000; 25(7):689-96.
Geoghegan et al., "Site-directed conjugation of nonpeptide groups to peptides and proteins via periodate oxidation of a 2-amino alcohol. Application to modification at N-terminal serine" Bioconjugate Chem, Mar.-Apr. 1992; 3(2):138-46.
Gilbert et al., "Useful proteins from recombinant bacteria" Sci American, Apr. 1980, 242(4):74-94.
Grosschedl et al., "Introduction of a mu immunoglobulin gene into the mouse germ line: specific expression in lymphoid cells and synthesis of functional antibody" Cell, Oct. 1984; 38(3):647-58.
Gummert et al., "Newer immunosuppressive drugs: a review" J Am Soc Nephrol, Jun. 1999; 10(6):1366-80.
Hammer et al., "Diversity of alpha-fetoprotein gene expression in mice is generated by a combination of separate enhancer elements" Science, Jan. 2, 1987; 235(4784):53-8.
Hanahan, "Heritable formation of pancreatic beta-cell tumours in transgenic mice expressing recombinant insulin/simian virus 40 oncogenes" Nature, May 9-15, 1985; 315(6015):115-22.
Haris et al., "Dynamic contrast-enhanced (DCE) derived transfer coefficient (ktrans) is a surrogate marker of matrix metalloproteinase 9 (MMP-9) expression in brain tuberculomas" J Magn Reson Imaging, Sep. 2008; 28(3):588-97.
Harvey et al., "Proposal for a standard system for drawing structural diagrams of N- and O-linked carbohydrates and related compounds" Proteomics, Aug. 2009; 9(15):3796-801.
Henry, "Cyclosporine and tacrolimus (FK506): A comparison of efficacy and safety profiles" Clin Transplantation, Jun. 1999; 13(3):209-20.
Hermanson, Bioconjugate Techniques, Academic Press: San Diego, CA. 1996. Cover page, title page, table of contents, and pp. 234-242.
Herrera-Estrella et al., "Expression of chimaeric genes transferred into plant cells using a Ti-plasmid-derived vector" Nature (Lond.), May 19, 1983; 303(5914):209-13.
Herrera-Estrella et al., "Light-inducible and chloroplast-associated expression of a chimaeric gene introduced into Nicotiana tabacum using a Ti plasmid vector" Nature, Jul. 12-18, 1984; 310(5973):115-20.
Hong et al., "Immunosuppressive Agents in Organ Transplantation: Past, Present, and Future" Seminars in Nephrology, Mar. 2000; 20(2):108-25.
Ideguchi et al., "Local adenovirus-mediated CTLA4-immunoglobulin expression suppresses the immune responses to adenovirus vectors in the brain" Neuroscience, 2000; 95(1):217-26.
Ito et al., "Induction of CTL responses by simultaneous administration of liposomal peptide vaccine with anti-CD40 and anti-CTLA-4 mAb" J Immunol, Feb. 1, 2000; 164(3):1230-5.
Johanson et al., "Multiplicity of cerebrospinal fluid functions: New challenges in health and disease" Cerebrospinal Fluid Res, May 14, 2008; 5:10.

(56) References Cited

OTHER PUBLICATIONS

Jong et al., "Dimethylmethylene blue-based spectrophotometry of glycosaminoglycans in untreated urine: a rapid screening procedure for mucopolysaccharidoses" Clin Chem, 1989; 35:1472.
Karlin et al., "Methods for assessing the statistical significance of molecular sequence features by using general scoring schemes" Proc Natl Acad Sci USA, Mar. 1990; 87(6):2264-8.
Karlin et al., "Applications and statistics for multiple high-scoring segments in molecular sequences" Proc Natl Acad Sci USA, Jun. 15, 1993; 90(12):5873-7.
Kelsey et al., "Species- and tissue-specific expression of human alpha 1-antitrypsin in transgenic mice" Genes and Devel, Apr. 1987; 1(2):161-71.
Kollias et al., "Regulated expression of human A gamma-, beta-, and hybrid gamma beta-globin genes in transgenic mice: manipulation of the developmental expression patterns" Cell, Jul. 4, 1986; 46(1):89-94.
Krumlauf et al., "Developmental regulation of alpha-fetoprotein genes in transgenic mice" Mol Cell Biol, Jul. 1985; 5(7):1639-48.
Kurlberg et al., "Blockade of the B7-CD28 Pathway by CTLA4-Ig Counteracts Rejection and Prolongs Survival in Small Bowel Transplantation" Scand J Immunol, Mar. 2000; 51(3):224-30.
Leder et al., "Consequences of widespread deregulation of the c-myc gene in transgenic mice: multiple neoplasms and normal development" Cell, May 23, 1986; 45(4):485-95.
Leriche et al., "Cleavable linkers in chemical biology" Bioorg Med Chem, Jan. 15, 2012; 20(2):571-82. Epub Jul. 30, 2011.
Link et al., "Principles of albumin and IgG analyses in neurological disorders. III. Evaluation of IgG synthesis within the central nervous system in multiple sclerosis" Scand J Clin Lab Invest, Sep. 1977; 37(5):397-401.
MacDonald, "Expression of the pancreatic elastase I gene in transgenic mice" Hepatology, Jan.-Feb. 1987; 7(1 Suppl):42S-51S.
Magram et al., "Developmental regulation of a cloned adult beta-globin gene in transgenic mice" Nature, May 23-29, 1985; 315(6017):338-40.
Marinova-Mutafchieva et al., "A comparative study into the mechanisms of action of anti-tumor necrosis factor alpha, anti-CD4, and combined anti-tumor necrosis factor alpha/anti-CD4 treatment in early collagen-induced arthritis" Arthritis Rheum, Mar. 2000; 43(3):638-44.
Marsh et al., "4-Methylumbelliferyl alpha-N-acetylglucosaminidase activity for diagnosis of Sanfilippo B disease" Clinical Genetics, 1985, 27: 258-262.
Mason et al., "The hypogonadal mouse: reproductive functions restored by gene therapy" Science, Dec. 12, 1986; 234(4782):1372-8.
Meikle et al., "Diagnosis of lysosomal storage disorders: evaluation of lysosome-associated membrane protein LAMP-1 as a diagnostic marker" Clin Chem, Aug. 1997; 43(8 Pt 1):1325-35.
Moder, "New medications for use in patients with rheumatoid arthritis" Ann Allergy Asthma Immunol, Mar. 2000; 84(3):280-4; quiz 284, 287.
Mundt et al., *Graff's Textbook of Routine Urinalysis and Body Fluids*, Lippincott Williams and Wilkins: Philadelphia, PA; 2010. Cover page, title page and table of contents.
Nagaraja et al., "Multiparametric magnetic resonance imaging and repeated measurements of blood-brain barrier permeability to contrast agents" Methods Mol Biol, 2011; 686:193-212.
Nevins, "Overview of new immunosuppressive therapies" Curr Opin Pediatr, Apr. 2000; 12(2):146-50.
Ornitz et al., "Elastase I promoter directs expression of human growth hormone and SV40 T antigen genes to pancreatic acinar cells in transgenic mice" Cold Spring Harbor Symp Quant Biol, 1985; 50:399-409.
Osol et al., *Remington's pharmaceutical sciences. 14th Edition.*, Mack Publishing Co.: Easton, PA; 1970. Cover page, title page and table of contents.

Osol et al., *Remington's pharmaceutical sciences. 18th Edition.*, Mack Publishing Co.: Easton, PA; 1990. Cover page, title page and table of contents.
Park et al., "The kinetics of blood brain barrier permeability and targeted doxorubicin delivery into brain induced by focused ultrasound" J Control Release, Aug. 20, 2012; 162(1):134-42. Epub Jun. 15, 2012.
Patlak et al., "Graphical Evaluation of Blood-to-Brain Transfer Constants from Multiple-Time Uptake Data" J Cereb Blood Flow Metab, Mar. 1983; 3(1):1-7.
Pinkert et al., "An albumin enhancer located 10 kb upstream functions along with its promoter to direct efficient, liver-specific expression in transgenic mice" Genes Dev, May 1987; 1(3):268-76.
Ponticelli et al., "Promising New Agents in the Prevention of Transplant Rejection" Drugs R D, Jan. 1999; 1(1):55-60.
Potter et al., "Review—The Use of Immunosuppressive Agents to Prevent Neutralizing Antibodies Against a Transgene Product" Ann N Y Acad Sci, Jun. 18, 1999; 875:159-74.
Przepiorka et al., "A Phase II Study of BTI-322, a Monoclonal Anti-CD2 Antibody, for Treatment of Steroid-Resistant Acute Graft-Versus-Host" Blood, Dec. 1, 1998; 92(11):4066-71.
Qi et al., "Effect of tacrolimus (FK506) and sirolimus (rapamycin) mono- and combination therapy in prolongation of renal allograft survival in the monkey" Translplantation, Apr. 15, 2000; 69(7):1275-83.
Readhead et al., "Expression of a myelin basic protein gene in transgenic shiverer mice: correction of the dysmyelinating phenotype" Cell, Feb. 27, 1987; 48(4):703-12.
Remington et al., *The Science and Practice of Pharmacy, 21st ed.* Lippincott Williams & Wilkins, Philadelphia, PA, 2006. Cover page, title page and table of contents.
Sambrook et al., *Molecular Cloning: A Laboratory Manual*, 2nd edition, Spring Harbor Laboratory Press, Cold Spring Harbor, NY, 1989. Cover page, title page and table of contents.
Sambrook et al., *Molecular Cloning: A Laboratory Manual*, Cold Spring Harbor Laboratory Press, Cold Spring Harbor, NY, 2001. Cover page, title page and table of contents.
Schliep et al., "Serum-CSF protein gradients, the blood-GSF barrier and the local immune response" J Neurol, May 18, 1978; 218(2):77-96.
Shani, "Tissue-specific expression of rat myosin light-chain 2 gene in transgenic mice" Nature, Mar. 21-27, 1985; 314(6008):283-6.
Skoog et al., "A population study on blood-brain barrier function in 85-year-olds: Relation to Alzheimer's disease and vascular dementia" Neurology, Apr. 1998; 50(4):966-71.
Slavik et al., "CD28/CTLA-4 and CD80/CD86 families: signaling and function" Immunol Res, 1999; 19(1):1-24.
Song et al., "Blood-brain barrier impairment is functionally correlated with clinical severity in patients of multiple system atrophy" Neurobiol Aging, Dec. 2011; 32(12):2183-9. Epub Feb. 10, 2010.
Sourbron et al., "Quantification of Cerebral Blood Flow, Cerebral Blood Volume, and Blood-Brain-Barrier Leakage with DCE-MRI" Magn Reson Med, Jul. 2009; 62(1):205-17.
Sourbron et al., "On the Scope and Interpretation of the Tofts Models for DCE-MRI" Magn Reson Med, Sep. 2011; 66(3):735-45. Epub Mar. 7, 2011.
Swift et al., "Tissue-specific expression of the rat pancreatic elastase I gene in transgenic mice" Cell, Oct. 1984; 38(3):639-46.
Takahashi et al., "Core fucose and bisecting GlcNAc, the direct modifiers of the N-glycan core: their functions and target proteins" Carbohydrate Research, Aug. 17, 2009; 344(12):1387-90. Epub May 4, 2009.
Tibbling et al., "Principles of albumin and IgG analyses in neurological disorders. I. Establishment of reference values" Scand J Clin Lab Invest, Sep. 1977; 37(5):385-90.
Tofts et al., "Modeling tracer kinetics in dynamic Gd-DTPA MR imaging" J Magn Reson Imaging, Jan.-Feb. 1997; 7(1):91-101.
Tofts et al., "Estimating Kinetic Parameters From Dynamic Contrast-Enhanced T I-Weighted MRI of a Diffusable Tracer: Standardized Quantities and Symbols" J Magn Reson Imaging, Sep. 1999; 10(3):223-32.
Villa-Kamaroff et al., "A bacterial clone synthesizing proinsulin" Proc Natl Acad Sci USA, Aug. 1978; 75(8):3727-31.

(56) References Cited

OTHER PUBLICATIONS

Wada, "Blood-brain barrier permeability of the demented elderly as studied by cerebrospinal fluid-serum albumin ratio" Intern Med, Jun. 1998; 37(6):509-13.

Wagner et al., "Nucleotide sequence of the thymidine kinase gene of herpes simplex virus type 1" Proc Natl Acad Sci USA, Mar. 1981; 78(3):1441-5.

Wang et al., "Vascular Volume and Blood-Brain Barrier Permeability Measured by Dynamic Contrast Enhanced MRI in Hippocampus and Cerebellum of Patients with MCI and Normal Controls" J Magn Reson Imaging, Sep. 2006; 24(3):695-700.

Weber et al., "Expression and Characterization of Human Recombinant and a-N-Actylglucosaminidase" Protein Expr Purif, Mar. 2001; 21(2):251-9.

Wilson et al., "The structure of an antigenic determinant in a protein" Cell, Jul. 1984; 37(3):767-778.

Wiseman et al., "Daclizumab: A Review of its Use in the Prevention of Acute Rejection in Renal Transplant Recipients" Drugs, Dec. 1999; 58(6):1029-42.

Wong, *Chemistry of Protein Conjugation and Cross Linking*, CRC Press LLC, Boca Raton, FL, 1991; Cover page, title page and table of contents.

Yamamoto et al., "Identification of a functional promoter in the long terminal repeat of Rous sarcoma virus" Cell, Dec. 1980; 22(3):787-97.

Yogalingam et al., "Mucopolysaccharidosis type IIIB: characterisation and expression of wild-type and mutant recombinant K-N-acetylglucosaminidase and relationship with Sancɸlippo phenotype in an attenuated patient" Biochim Biophys Acta, Nov. 15, 2000; 1502(3):415-25.

Zhao et al., "Purification and characterization of recombinant human alpha-N-acetylglucosaminidase secreted by Chinese hamster ovary cells" Protein Expr Purif, Jun. 2000; 19(1):202-11.

International Patent Application No. PCT/US2017/015646, filed Jan. 30, 2017; International Preliminary Report on Patentability dated Aug. 9, 2018; 9 pages.

\* cited by examiner

SEQUENCE LISTING

```
<160> NUMBER OF SEQ ID NOS: 1

<210> SEQ ID NO 1
<211> LENGTH: 743
<212> TYPE: PRT
<213> ORGANISM: Homo sapiens

<400> SEQUENCE: 1

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
    50                  55                  60

Tyr Ser Leu Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
                130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
                210                 215                 220
```

```
Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640
```

-continued

```
Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665             670

Pro Arg Trp Arg Leu Phe Leu Glu Ala Leu Val Asp Ser Val Ala Gln
        675                 680             685

Gly Ile Pro Phe Gln Gln His Gln Phe Asp Lys Asn Val Phe Gln Leu
    690             695                 700

Glu Gln Ala Phe Val Leu Ser Lys Gln Arg Tyr Pro Ser Gln Pro Arg
705             710                 715                 720

Gly Asp Thr Val Asp Leu Ala Lys Lys Ile Phe Leu Lys Tyr Tyr Pro
            725             730                 735

Arg Trp Val Ala Gly Ser Trp
            740
```

METHODS OF TREATING MUCOPOLYSACCHARIDOSIS IIIB (MPSIIIB)

RELATED APPLICATIONS

This application is the § 371 U.S. National Stage of International Application No. PCT/US2015/052921, filed Sep. 29, 2015, which claims the benefit of U.S. Provisional Application No. 62/057,030, filed Sep. 29, 2014, the disclosures of which are incorporated by reference herein in their entireties.

SEQUENCE LISTING

This application contains a Sequence Listing electronically submitted via EFS-Web to the United States Patent and Trademark Office, in its capacity as Receiving Office, on Sep. 29, 2015, as an ASCII text file named "089WO_SEQ_list.txt", and an amended Sequence Listing electronically submitted via EFS-Web to the United States Patent and Trademark Office, in its capacity as Receiving Office, on Nov. 2, 2015, as an ASCII text file entitled "SYN089WO_Corrected_SEQ.txt" having a size of 7 kilobytes. The information contained in the Sequence Listing is incorporated by reference herein.

BACKGROUND

Sanfilippo Syndrome B, also known as Mucopolysaccharidosis IIIB (MPSIIIB), is an autosomal recessive lysosomal storage disease (LSD) caused by mutations in the Naglu gene on human chromosome 7, which encodes a lysosomal enzyme known as N-acetyl-alpha-D-glucosaminidase (NaGlu). NaGlu is required for the degradation of heparan sulfate (HS) as part of the stepwise breakdown of glycosaminoglycans (GAG) in the lysosome. The deficiency or absence of NaGlu leads to accumulation and urinary excretion of heparan sulfate, resulting in severe central nervous system (CNS) abnormalities as well as mild systemic organ dysfunction; the effects on neurons in the CNS lead to delayed development, progressive mental retardation, neurological dysfunction, severe dementia, and early mortality. With over 70 different mutations identified to date, Sanfilippo Syndrome B exhibits extensive molecular and genetic heterogeneity.

The function of blood brain barrier (BBB) is to control cerebral homeostasis by selective transport of molecules and cells from the systemic compartment. The BBB is made up of structural components of the microvasculature endothelial cells of brain capillaries, epithelial cells of the choroids plexus, astrocytes end feet, and pericytes. Endothelial cells are connected via tight junction and adherens thereby forming a diffusion barrier.

Compromised blood-brain barrier (BBB) has been demonstrated in an animal model of MPSIIIB (Garbuzova-Davis et al., PLoS ONE 6(3): e16601 (2011)) as well as in human patients with MPSIIIA and MPSIIIC, closely related conditions that result from different enzyme deficiencies but that share the accumulation of HS and have common neuropathological manifestations (Garbuzova-Davis et al., BMC Neurology 13:174 (2013)). However, little is known about the condition of the BBB in MPS IIIB human patients.

This presents the problem of whether enzyme replacement therapy involving systemic delivery (e.g., intravenous administration) of recombinant human NaGlu enzyme which requires penetration of BBB in MPS IIIB patients can exert efficacy in the brain (CNS) as the disease is being treated and as a potential BBB dysfunction, if any, is being ameliorated. Therefore, a need exists for the safe and effective treatment of MPS IIIB from the systemic initial dosing to maintenance therapy in the CNS of MPS IIIB patients in accordance with their BBB structure and function as well as the kinetics of HS accumulation in the CNS that affects neurocognition and motor skills.

SUMMARY

Methods for treating NaGlu associated diseases, e.g., MPS IIIB, using recombinant human NaGlu protein (rhNaGlu) that contains glycosylation patterns that allow rhNaGlu to effectively cross the BBB and be taken up into cells within the CNS of animals deficient in NaGlu have been described in PCT/US12/59708. The invention is based on the discovery that rhNaGlu described herein can effectively cross even intact BBB in normal healthy mammalian subjects, not affected or impaired by any CNS disorder or condition. Thus, described herein are methods for the initial dosing regimen and subsequent maintenance of therapeutic levels of rhNaGlu in the central nervous system (e.g., brain tissue) in a mammal undergoing long-term enzyme replacement therapy with rhNaGlu for treating NaGlu-associated diseases, e.g., MPS IIIB, using intravenous administration of rhNaGlu.

In a first aspect the invention provides methods for treating the central nervous system (CNS) in a human patient with mucopolysaccharidosis (MPS) IIIB undergoing long-term enzyme replacement therapy with recombinant human N-acetyl-alpha-D-glucosaminidase (rhNaGlu). The methods include intravenously administering to said patient a therapeutically effective amount of rhNaGlu to prevent reaccumulation of heparan sulfate levels in cerebrospinal fluid (CSF), wherein the intravenous administration prevents reaccumulation of heparan sulfate levels in the CSF.

In some embodiments, rhNaGlu is intravenously administered at a first dose periodically for a first period, and intravenously at a second dose periodically for a second period. In one embodiment, there can be a washout period between the first period and the second period that the patient does not receive any rhNaGlu therapy. In one embodiment, the treatment under the first period reduces heparan sulfate (HS) levels (e.g., in the CSF) at least 20%, at least 30%, at least 40%, at least 50%, at least 60%, at least 70%, at least 80% or at least 90% from pretreatment levels. In a preferred embodiment, the treatment under the first period reduces HS levels (e.g., in the CSF) at least 50% from pretreatment levels. In one embodiment, the treatment under the second period is to maintain or further reduce the HS levels (e.g., in the CSF) from those of the first period. In a preferred embodiment, the patient is dosed during the first period more frequently than during the second period. In one embodiment, the amount of rhNaGlu administered per infusion or injection in the first period and the amount of rhNaGlu administered in per infusion or injection in the second period can be the same, but the administration is less frequent in the second period. In one embodiment, the amount of the first dose (in a dose) is higher than amount of the second dose. For example, the first dose in the first period is about 0.1 mg/kg body weight, about 0.3 mg/kg body weight, about 0.5 mg/kg body weight, about 1 mg/kg body weight, 3 mg/kg body weight, about 5 mg/kg body weight, about 8 mg/kg body weight, about 10 mg/kg body weight, about 15 mg/kg body weight, about 20 mg/kg body weight, about 25 mg/kg body weight, about 30 mg/kg body weight, about 35 mg/kg body weight, about 40 mg/kg body weight, about 50 mg/kg body weight per infusion or injection. The second dose can be about 0.5 mg/kg body weight, about 1 mg/kg body weight, 3 mg/kg body weight, about 5 mg/kg body weight, about 8 mg/kg body weight, about 10 mg/kg body weight, about 15 mg/kg body weight, about 20 mg/kg body weight, about 25 mg/kg body weight, about 30 mg/kg body weight, about 35 mg/kg body weight, about 40 mg/kg body weight, about 50 mg/kg body weight per infusion or injection. In one embodiment, the first dose is administered one time about 7 days to one time of about 30 days. In one embodiment, the first dose is administered one time about 7 days. In one embodiment, the first dose is administered one time about 10 days. In one embodiment, the first dose is administered one time about 14 days. In one embodiment, the first dose is administered one time about 30 days. In one embodiment, once the CSF HS level is reduced at least, for example, 50%, 60%, 70%, 80% or more from the pretreatment level, the patient is not dosed for about 1 month, about 2 months, about 3 months, about 4 months, about 5 months or about 6 months before the second dose initiates. In one embodiment, the second dose is administered less frequently than the first dose, for example, one time about 10 days to one time of about 60 days. In one embodiment, the second dose is administered one time about 14 days or one time about 90 days. In a preferred embodiment, the second dose is administered one time about 14 days or one time about 30 days.

As used herein an intact BBB means that the BBB has permeability levels within the range of levels represented by normal, healthy subjects of a similar age, i.e., has permeability equivalent to a normal, healthy subject of a similar age. Whether the patient has an intact blood brain barrier (BBB) can be determined by a CSF/serum albumin Index; a CSF/serum IgG Index; a CSF IgG Index; and/or a dynamic contrast-enhanced magnetic resonance imaging (DCEMRI). In some embodiments, the patient has been treated with rhNaGlu (e.g., administered intravenously or intrathecally) prior to the present treatment, e.g., for at least three months, at least six months, at least nine months, or at least one year. In some embodiments, the patient is at the age of about 7 or younger and/or has a CSF/serum albumin Index of less than about 5 and/or a CSF/IgG Index of less than about 0.7.

In some embodiments, the methods include determining one or more of $K^{trans}$, a CSF/serum albumin Index, a CSF/serum IgG Index, and/or a CSF IgG Index in the subject, and selecting the subject based on the presence of a $K^{trans}$ no more than 125% of a reference $K^{trans}$ that represents an intact BBB in a normal healthy subject, a CSF/serum albumin Index below 15, and/or a CSF/serum IgG Index less than 10, and/or a CSF IgG Index.

In some embodiments, the patient has a $K^{trans}$ equal to or less than a reference $K^{trans}$ that represents an intact BBB in a normal healthy subject, CSF/serum albumin index less than 10, or less than 9; or has a CSF/serum IgG Index less than 8; or has a CSF IgG Index less than 0.85.

In some embodiments, the rhNaGlu comprises M6P and bisecting GlcNAc. In some embodiments, the rhNaGlu comprises at least 1 mol of M6P per mol of rhNaGlu. In some embodiments, the rhNaGlu comprises about 2 to about 4 bisecting GlcNAc-containing oligosaccharide structures per molecule of protein.

In some embodiments, the rhNaGlu comprises a sufficient amount of M6P or bis-M6P for uptake into a cell of the CNS having a M6P receptor on the cell surface. In certain embodiments, M6P is present at a concentration that is greater than about 0.5, about 1, about 2, about 3, about 4, about 5 or about 6 mole(s) per mole of protein. In other embodiments, the rhNaGlu is not sialylated, or at most carry 1, 2, 3, 4, or 5 sialic acid residues per protein.

In another aspect, the invention provides methods for treating the central nervous system (CNS) in a human patient with mucopolysaccharidosis (MPS) IIIB, wherein said patient has an intact blood brain barrier (BBB) as determined by: a CSF/serum albumin Index; a CSF/serum IgG Index; a CSF IgG Index; and/or a dynamic contrast-enhanced magnetic resonance imaging (DCEMRI). The methods include intravenously administering to said patient a therapeutically effective amount of rhNaGlu to prevent the progression of one or more neurological symptoms of Sanfilippo Syndrome B in the human patient, wherein the intravenous administration ameliorates one or more neurological symptoms of Sanfilippo Syndrome B. In one embodiment, the rhNaGlu comprises a sufficient amount of M6P or bis-M6P for uptake into a cell of the CNS having a M6P receptor on the cell surface. In one embodiment, M6P is present at a concentration that is greater than about 0.5, 1, about 2, about 3, about 4, about 5 or about 6 mole(s) per mole of protein. In another embodiment, the rhNaGlu is not sialylated, or at most carry 1, 2, 3, 4, or 5 sialic acid residues per protein.

In another aspect, the invention provides methods for treating the central nervous system (CNS) in a human patient with MPS IIIB undergoing long-term enzyme replacement therapy with the rhNaGlu, the method comprising intravenously administering to said patient a therapeutically effective amount of rhNaGlu to prevent reaccumulation of heparan sulfate levels in cerebrospinal fluid (CSF), wherein said patient has an intact BBB, and wherein the intravenous administration prevents reaccumulation of heparan sulfate levels in the CSF.

In some embodiments, the therapeutically effective amount is sufficient to ameliorate one or more neurological symptoms of Sanfilippo Syndrome B in the subject.

In some embodiments, the one or more neurological symptoms of Sanfilippo Syndrome B in the human patient is delayed development of speech, progressive mental retardation, neurological dysfunction, delayed neurocognitive and development function or dementia. In some embodiments, the delayed neurocognitive and development function is determined by patient's scores on one or more tests selected from the group consisting of Vineland-II, the Bayley Scales of Infant and Toddler Development and Kaufman Assessment Battery for Children.

In some embodiments, the one or more neurological symptoms of Sanfilippo Syndrome B in the human patient is determined by assessment of caregiver quality of life, assessment of language, or neurocognitive and developmental function. In some embodiments, the caregiver quality of life is determined by Zarit Burden Interview. In some embodiments, the assessment of language is determined by Children's Communication Checklist.

In some embodiments, the one or more neurological symptoms of Sanfilippo Syndrome B in the human patient is a sleep disorder assessed by the Children's Sleep Habits Questionnaire.

In some embodiments, the methods described herein include administering a dose of between 1 mg/kg and 50 mg/kg rhNaGlu.

In some embodiments, the subject has: a CSF/serum albumin Index below about 15, below about 9, below about 7 or below about 5; a CSF/serum IgG ratio less than about 10, or less than about 8; a CSF IgG Index of less than about 0.9 or less than about 0.7; and/or a $K^{trans}$ no more than about 125% of a reference $K^{trans}$ that represents an intact BBB in a normal healthy subject.

In another aspect, the invention provides methods for treating the central nervous system (CNS) in a human patient with MPS IIIB undergoing long-term enzyme replacement therapy with recombinant human N-acetyl-alpha-D-glucosaminidase (rhNaGlu), the method comprising intravenously administering to said patient a therapeutically effective amount of rhNaGlu to suppress or prevent reaccumulation of hepatocyte growth factor (HGF) levels in cerebrospinal fluid (CSF), wherein said patient has an intact blood brain barrier (BBB), and wherein the intravenous administration prevents reaccumulation of HGF levels in the CSF.

DETAILED DESCRIPTION

Definitions

Figure 1:
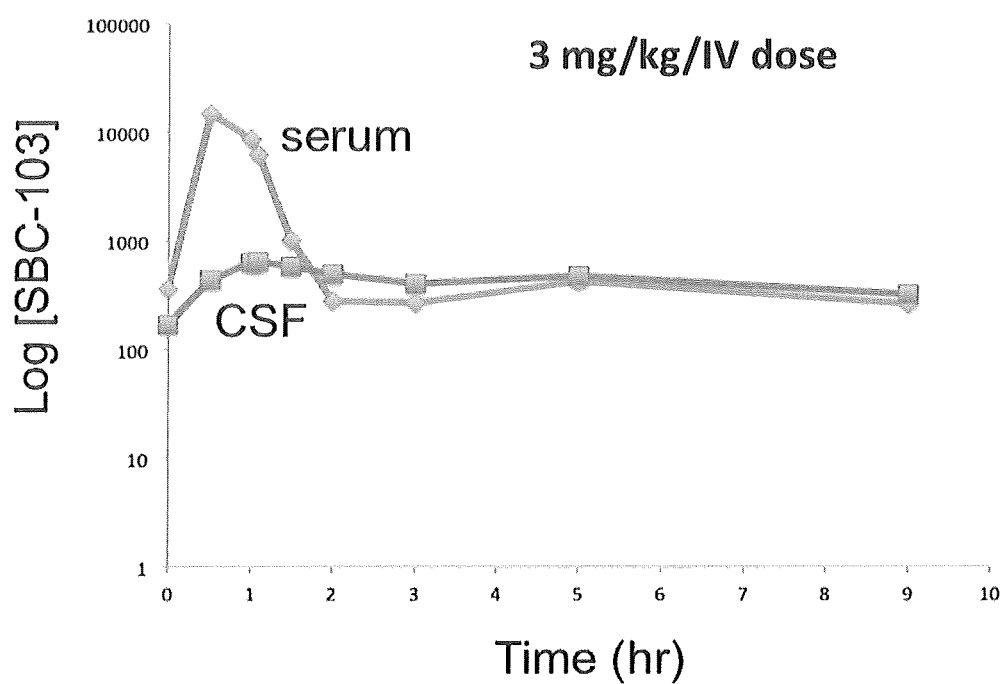
FIG. 1 shows levels of rhNaGlu in serum and CSF after IV administration at 3 mg/kg/dose.

Some of the definitions and abbreviations used herein include the following: aa, amino acid(s); bp, base pair(s); CDS, coding sequence cDNA, DNA complementary to an RNA; GalNac, N-acetylgalactosamine; Gal, galactose; GlcNac, N-acetylglucosamine; nt, nucleotide(s); kb, 1,000 base pairs; μg, microgram; mL, milliliter; ng, nanogram; and nt, nucleotide.

Certain definitions are set forth herein to illustrate and define the meaning and scope of the various terms used to describe the invention herein.

The term "avian" as used herein refers to any species, subspecies or strain of organism of the taxonomic class ava, such as, but not limited to, chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partridge-colored), as well as strains of turkeys, pheasants, quails, duck, ostriches and other poultry commonly bred in commercial quantities.

The phrases "based on" and "derived from" typically mean obtained from, in whole or in part. For example, a retroviral vector being based on or derived from a particular retrovirus or based on a nucleotide sequence of a particular retrovirus mean that the genome of the retroviral vector contains a substantial portion of the nucleotide sequence of the genome of the particular retrovirus.

Nucleotide sequences that are not naturally part of a particular organism's genome or are introduced at a non-native site in the organism's genome are referred to as "foreign" nucleotide sequences, "heterologous" nucleotide sequences, "recombinant" nucleotide sequences or "exogenous" nucleotide sequences. In addition, a nucleotide sequence that has been isolated and then reintroduced into the same type (e.g., same species) of organism is not considered to be a naturally occurring part of a particular organism's genome and is therefore considered exogenous or heterologous. "Heterologous proteins" or "exogenous proteins" can be proteins encoded by foreign, heterologous or exogenous nucleotide sequences and therefore are often not naturally expressed in a cell of the host organism.

As used herein, the terms "exogenous," "heterologous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, DNA that encodes a gene product or gene product(s) of interest, for example, for production of an encoded protein. The terms "heterologous" and "exogenous" can also refer to a biomolecule such as a protein which is not normally found in a certain cell, tissue or substance produced by an organism or is not normally found in a certain cell, tissue or substance produced by an organism in an amount or location the same as that found to occur naturally. For example, a protein that is heterologous or exogenous to an egg is a protein that is not normally found in the egg.

The term "expressed" or "expression" as used herein refers to the transcription of a coding sequence to yield an RNA molecule at least complementary in part to a region of one of the two nucleic acid strands of the coding sequence. The term "expressed" or "expression" as used herein can also refer to the translation of an mRNA to produce a protein or peptide.

The term "expression vector" as used herein refers to a nucleic acid vector that comprises a gene expression controlling region, such as a promoter or promoter component, operably linked to a nucleotide sequence encoding at least one polypeptide.

The term "fragment" as used herein can refer to, for example, an at least about 10, 20, 50, 75, 100, 150, 200, 250, 300, 500, 1000, 2000, 5000, 6000, 8000, 10000, 20000, 30000, 40000, 50000 or 60000 nucleotide long portion of a nucleic acid that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein can also refer to, for example, an at least about 5, 10, 15, 20, 25, 30, 40, or 50 amino acid residues less than a full length amino acid sequence for NaGlu (i.e., amino acid sequence 24-743 of SEQ ID NO:1), which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 50%, about 60%, about 70%, about 80%, about 90%, about 95% or about 99% of a particular nucleotide sequence or amino acid sequence.

The term "fully transgenic" or "germline transgenic" refers to an animal such as an avian that contains at least one copy of a transgene in essentially all of its cells.

As used herein, "host cells" refers to cells that harbor vectors constructed using recombinant DNA techniques and encoding at least one heterologous gene.

As used herein, the terms "glycan," "glycan structure," "glycan moiety," "oligosaccharide," "oligosaccharide structure," "glycosylation pattern," "glycosylation profile," and "glycosylation structure" have essentially the same meaning and each refers to one or more structures which are formed from sugar residues and are attached to glycosylated protein such as rhNaGlu. For example, "N-glycan" or "N-linked glycan" refers to a glycan structure attached to a nitrogen of asparagine or arginine side-chain of the glycosylated protein. "O-glycan" or "O-linked glycan" refers to a glycan structure attached to the hydroxyl oxygen of serine, threonine, tyrosine, hydroxylysine, or hydroxyproline side chain of the glycosylate protein.

"Overexpression", as used herein, refers to the production of a gene product in transgenic organisms that exceeds levels of production in normal or non-transformed organisms.

The term "oviduct" or "oviduct tissue" refers to a tissue of an avian oviduct, such as the magnum, e.g., tubular gland cells, where proteins are produced with N-linked oligosaccharides that contain increased amounts of mannose and mannose-6-phosphate (e.g., M6P or bis-M6P) and substantially reduced amounts of galactose and/or sialic acid relative to that of proteins produced in other tissue of the avian such as liver or kidney tissue.

The term "oviduct-specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of oviduct specific promoters include, but are not limited to, ovalbumin promoter, ovomucoid promoter, ovoinhibitor promoter, lysozyme promoter and ovotransferrin promoter and functional portions of these promoters, e.g., promoter components. By limiting the expression of NaGlu protein to the magnum using oviduct specific promoters, deleterious physiological effects to the bird as result of expression of these enzymes in other tissues of the bird can be minimized.

The terms "percent sequence identity," "percent identity," "% identity," "percent sequence homology," "percent homology," "% homology" and "percent sequence similarity" can each refer to the degree of sequence matching between two nucleic acid sequences or two amino acid sequences. Such sequence matching can be determined using the algorithm of Karlin & Altschul (1990) Proc. Natl. Acad. Sci. 87: 2264-2268, modified as in Karlin & Altschul (1993) Proc. Natl. Acad. Sci. 90: 5873-5877. Such an algorithm is incorporated into the NBLAST and XBLAST programs of Altschul et al. (1990) T. Mol. Biol. Q15: 403-410. BLAST nucleotide searches are performed with the NBLAST program, score=100, wordlength=12, to obtain nucleotide sequences homologous to a nucleic acid molecule as described herein. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Altschul et al. (1997) Nucl. Acids Res. 25: 3389-3402. When utilizing BLAST and Gapped BLAST programs, the default parameters of the respective programs (e.g., XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons. A sequence may be at least 50%, 60%, 70%, 75%, 80%, 85%, 90%, 91%, 92%, 93%, 94%, 95%, 96%, 97%, 98%, 99% or more identical to another sequence, e.g., the NaGlu protein sequence identified herein.

The term "avian derived" refers to a composition or substance produced by or obtained from a bird, poultry or avian. "Avian" refers to birds that can be kept as livestock, including but not limited to, chickens, ducks, duck, turkey, quail and ratites. For example, "avian derived" can refer to chicken derived, turkey derived and/or quail derived.

As the term "promoter" as used herein refers to a DNA sequence useful to initiate transcription by an RNA polymerase in an avian cell. A "promoter component" is a DNA sequence that can, by itself or in combination with other DNA sequences, effect or facilitate transcription. Promoter components can be functional fragments of promoters.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

A "therapeutic protein" or "pharmaceutical protein" is a substance that, in whole or in part, makes up a drug. In particular, "therapeutic proteins" and "pharmaceutical proteins" include an amino acid sequence which in whole or in part makes up a drug.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with certain concentrations of salt, for example, but without limitation, a calcium or magnesium salt, or exposing the cells to an electric field, detergent, or liposome material, to render the host cell competent for the uptake of the nucleic acid molecules.

As used herein, a "transgenic animal" is any non-human animal, such as an avian species, including the chicken, in which one or more of the cells of the animal contain heterologous nucleic acid introduced by way of human intervention, such as by transgenic techniques known in the art (see, for example, U.S. patent publication No. 2007/0243165, published Oct. 18, 2007, the disclosure of which is incorporated in its entirety herein by reference) including those disclosed herein. The nucleic acid is introduced into an animal, directly or indirectly by introduction into a cell (e.g., egg or embryo cell) by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule can be integrated within a chromosome, or it may be extrachromosomally replicating DNA. In the typical transgenic animal, the transgene can cause cells to express a recombinant form of the target protein or polypeptide. The terms "chimeric animal" or "mosaic animal" are used herein to refer to animals in which a transgene is found, or in which the recombinant nucleotide sequence is expressed, in some but not all cells of the animal. A germ-line chimeric animal contains a transgene in its germ cells and can give rise to an offspring transgenic animal in which most or all cells of the offspring will contain the transgene.

As used herein, the term "transgene" means a nucleic acid sequence (encoding, for example, a rhNaGlu protein) that is partly or entirely heterologous, i.e., foreign, to the animal or cell into which it is introduced, or, is partly or entirely homologous to an endogenous gene of the transgenic animal or cell into which it is introduced, but which is designed to be inserted, or is inserted, into the animal or cell genome in such a way as to alter the genome of the organism into which it is inserted (e.g., it is inserted at a location which differs from that of the natural gene or its insertion results in a knockout).

As used herein, the term "enzyme replacement therapy (ERT)" refers to a therapeutic strategy for correcting an enzyme deficiency in a subject by administering the missing enzyme to a subject. For lysosomal enzyme replacement therapy to be effective, the therapeutic enzyme must be delivered to lysosomes in the appropriate cells in tissues where the storage defect is manifested. In the present methods, the enzyme is administered to the subject systemically, e.g., intravenously, and is able to cross the blood brain barrier (BBB). Without intending to be limited by mechanism, it is believed that as the blood perfuses patient tissues, enzyme is taken up by cells and transported to the lysosome, where the enzyme acts to eliminate material that has accumulated in the lysosomes due to the enzyme deficiency.

The terms "treat," "treating," and "treatment" refer to methods of alleviating, abating, or ameliorating a disease or symptom, preventing an additional symptom, ameliorating or preventing an underlying cause of a symptom, inhibiting a disease or condition, arresting the development of a disease or condition, relieving a disease or condition, causing regression of a disease or condition, relieving a condition caused by the disease or condition, or stopping a symptom of the disease or condition either prophylactically and/or after the symptom has occurred, including stopping or preventing recurrence of a disease, condition or underlying cause of a symptom, or maintaining the patient in state of remission of a disease or condition.

As used herein, the term "subject" or "patient" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human subjects having a NaGlu deficiency or NaGlu associated disease.

As used herein a "NaGlu-associated disease" is a disease or condition which is mediated by NaGlu activity or is associated with aberrant NaGlu expression or activity. An example of an NaGlu associated disease includes, but is not limited to, NaGlu deficiency such as Sanflippo Syndrome B (also known as mucopolysaccharidosis type IIIB).

"Intravenous injection," often medically referred to as IV push or bolus injection, refers to a route of administration in which a syringe is connected to the IV access device and the medication is injected directly, typically rapidly and occasionally up to a period of 15 minutes if it might cause irritation of the vein or a too-rapid effect. Once a medicine has been injected into the fluid stream of the IV tubing, there must be some means of ensuring that it gets from the tubing to the patient. Usually this is accomplished by allowing the fluid stream to flow normally and thereby carry the medicine into the bloodstream. However, in some cases a second fluid injection, sometimes called a "flush," is used following the first injection to facilitate the entering of the medicine into the bloodstream. Intravenous administration is one type of systemic administration.

"Intravenous infusion" refers to a route of administration in which medication is delivered over an extended period of time. For example, the medication can be delivered to a patient over a period of time between 1 and 8 hours. The medication can also be delivered to a patient over a period of about 1, about 2, about 3, about 4, about 5, about 6, about 7, or about 8 hours. To accomplish an intravenous infusion, an IV gravity drip or an IV pump can be used. IV infusion is typically used when a patient requires medications only at certain times and does not require additional intravenous fluids (e.g., water solutions which can contain sodium, chloride, glucose, or any combination thereof) such as those that restore electrolytes, blood sugar, and water loss.

ABBREVIATIONS

BBB blood brain barrier
cDNA complementary DNA
CNS central nervous system
CSF cerebrospinal fluid
Fuc Fucose
GAG glycosaminoglycan
Gal Galactose
GalNAc N-Acetylgalactosamine
Glc Glucose
GlcNAc N-Acetylglucosamine
HGF hepatocyte growth factor
HS heparan sulfate
HSD heparan sulfate disaccharides
IV intravenous
IT intrathecal
Man mannose
M6P mannose-6-phosphate
MPSIIIB Mucopolysaccharidosis IIIB (Sanfilippo B Syndrome)
rhNaGlu recombinant human alpha-N-acetyl-glucosaminidase
NeuNAc N-acetylneuraminic acid Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Sanfilippo Syndrome B

Approximately 1 out of 200,000 births is affected by Sanfilippo Syndrome B and the deficiency mainly manifests in young children. After an initial symptom-free interval, patients suffering from Sanfilippo Syndrome B usually present with a slowing of mental development and behavioral problems, followed by progressive intellectual decline resulting in severe mental retardation, dementia and motor disease. Acquisition of speech is slow and incomplete. Profoundly affected patients may present delayed psychomotor and speech development as early as 2 years of age. The disease usually progresses to increasing behavioral disturbance and sleep disturbance. Although the clinical features are mainly neurological, patients often develop diarrhea, carious teeth, an enlarged liver and spleen, stiff joints, hirsuteness and/or coarse hair and may exhibit blood-clotting problems. In the final stage of the illness, patients become immobile and unresponsive and develop swallowing difficulties and seizure. The life-span of an affected child typically does not extend beyond late teens to early twenties.

Different approaches have been attempted to provide the missing enzyme in patients. To produce NaGlu for enzyme replacement therapy (ERT), human NaGlu has been expressed in various mammalian cell culture systems. However, in contrast to the naturally occurring NaGlu which trafficks to the lysosome intracellularly, rhNaGlu proteins produced and secreted from mammalian cells were found to contain no or only a trace amount of mannose-6-phosphate (M6P). The absence or scarcity of M6P moieties in the secreted mammalian cell derived recombinant NaGlu has been a problem in targeting the protein into the cell (e.g., human skin fibroblasts) via M6P receptor mediated endocytosis (see, Zhao et al., *Protein Expression and Purification*, 19:202-211 (2000); and Weber et al., *Protein Expression and Purification*, 21:251-259 (2001)). The low degree of phosphorylation was seen in secreted mouse NaGlu expressed in CHO cells, secreted human NaGlu expressed in HeLa cells, secreted human NaGlu expressed in human fibroblasts, and secreted human NaGlu expressed in human embryonic kidney (HEK) cell line 293 (see, Zhao et al., *Protein Expression and Purification*, 19:202-211 (2000); Yogalingam et al., *Biochim Biophys. Acta* 1502: 415-425; and Weber et al., *Protein Expression and Purification*, 21:251-259 (2001)). No or weak phosphorylation of N-glycans in the NaGlu proteins secreted from the mammalian cells has posed a major obstacle for the development of a rhNaGlu protein suitable for enzyme replacement therapy (see, Zhao et al., *Protein Expression and Purification*, 19:202-211 (2000)).

Moreover, direct administration of mammalian cell-produced rhNaGlu having the native amino acid sequence into the central nervous system (CNS) (e.g., intrathecal administration into the cerebrospinal fluid (CSF)) of NaGlu deficient mice has been attempted, but failed to demonstrate successful biodistribution of the enzyme to the brain due to lack of requisite M6P residues for efficient cellular uptake.

MPS IIIB patients have mildly leaky or compromised BBB integrity (see Example 3.2). Once initial treatment has been effective, such successful treatment might restore the function and integrity of the BBB, which might render a systemic administration, such as an intravenous route, less effective for a long-term therapy.

The invention is based on the discovery that rhNaGlu described herein can effectively cross even intact BBB in normal healthy mammalian subjects, not affected or impaired by any CNS disorder or condition. These findings provide a technical solution to the problem that stems from the belief that restoration of the BBB can render systemic administration routes less effective following the initial treatment of MPS IIIB. Because MPS IIIB deficiency is a genetic disorder that will likely require life-long enzyme replacement therapy, the ability to treat MPS IIIB patients in a systemic manner (e.g., intravenous administration) on a long-term basis achieves a significant advancement in patient care as it drastically enhances the quality of life for not only patients, but also care providers.

Methods of Treatment

The present invention provides methods of maintaining therapeutic levels of rhNaGlu for long-term treatment of NaGlu-associated diseases, e.g., Sanfilippo Syndrome B. Recombinant human NaGlu employed in accordance with the invention includes rhNaGlu which can be produced in any useful protein expression system including, without limitation, cell culture (e.g., CHO cells, COS cells), bacteria such as *E. coli*, transgenic animals such as mammals and avians (e.g., chickens, duck, and turkey) and in plant systems (e.g., duck weed and tobacco plants), provided that the rhNaGlu is expressed with or is otherwise modified to include the appropriate oligosaccharides as discussed in more detail below. In some embodiments, the recombinant NaGlu is produced in a transgenic animal, such as an avian. In one embodiment, the recombinant NaGlu is produced in a transgenic chicken.

Administration

The methods described herein include multiple administrations of a therapeutically effective amount of the rhNaGlu described herein over an extended period of time, e.g., after an initial treatment with the rhNaGlu has successfully lowered levels of HS in cells of the subject, e.g., for a time exceeding one week, two weeks, one month, two months, three months, four months, five months, six months, nine months, or one year. The rhNaGlu can be administered at regular intervals, depending on the nature, severity and extent of the subject's condition. In some embodiments, e.g., once the initial therapeutic effect has been achieved, an amount of the rhNaGlu protein sufficient to maintain therapeutically effective levels of rhNaGlu can be administered systemically (e.g., intravenously) periodically at regular intervals (e.g., once every year, once every six months, once every five months, once every three months, bimonthly (once every two months), monthly (once every month), biweekly (once every two weeks) or weekly).

"Therapeutically effective amount" or "therapeutically effective dose" as used herein refers to the dose (e.g., amount and/or interval) of drug required to produce an intended therapeutic response (e.g., reduction of heparan sulfate levels; increase in NaGlu activity in a target tissue such as the brain; maintenance of remission of MPS IIIB symptoms in the brain; or prevention of recurrence of MPS IIIB symptoms). A therapeutically effective dose refers to a dose that, as compared to a corresponding subject who has not received such a dose, results in improved treatment, healing, prevention, or amelioration of a disease, disorder, or side effect, or a decrease in the rate of the occurrence or recurrence or advancement of a disease or disorder. The term also includes within its scope, doses effective to enhance maintenance of remission of a disease, disorder, or symptom or to prevent recurrence of a disease, disorder, or symptom.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof. Generally, the amount of a therapeutic agent (e.g., the rhNaGlu as described herein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg bra body in weight. Ranges and values intermediate to the above recited ranges and values (e.g., 10-50 mg/kg, 1-5 mg/kg, 2-8 mg/kg, 5-10 mg/kg, 0.1-10 mg/kg, 0.3-30 mg/kg, 0.3-50 mg/kg, 0.5-10 mg/kg, 5-30 mg/kg, or 6-27 mg/kg) are also contemplated to be part of the invention.

In some embodiments, the therapeutically effective dose is greater than or at least about 0.1 mg/kg body weight, greater than or at least about 0.2 mg/kg body weight, greater than or at least about 0.3 mg/kg body weight, greater than or at least about 0.4 mg/kg body weight, greater than or at least about 0.5 mg/kg body weight, greater than or at least about 1.0 mg/kg body weight, greater than or at least about 3 mg/kg body weight, greater than or at least about 5 mg/kg body weight, greater than or at least about 6 mg/kg body weight, greater than or at least about 7 mg/kg body weight greater than or at least about 10 mg/kg body weight, greater than or at least about 15 mg/kg body weight, greater than or at least about 20 mg/kg body weight, greater than or at least about 30 mg/kg body weight, greater than or at least about 40 mg/kg body weight, greater than or at least about 50 mg/kg body weight, greater than or at least about 60 mg/kg body weight, greater than or at least about 70 mg/kg body weight, greater than about or at least 80 mg/kg body weight, greater than or at least about 90 mg/kg body weight, greater than or at least about 100 mg/kg body weight. Ranges and values intermediate to the above recited ranges and values are also contemplated to be part of the invention.

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5: 10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

In some embodiments, the methods include systemically, e.g., intravenously, administering to the subject a rhNaGlu containing a sufficient amount of oligosaccharides (e.g., mannose and phosphorylated mannose (i.e., M6P or bis-M6P)), in an amount sufficient to treat (e.g., reduce, ameliorate) or prevent one or more symptoms of a NaGlu deficiency or NaGlu-associated disease, after an initial treatment with the rhNaGlu has successfully lowered the levels of HS in CNS cells of the subject (as measured by, for example HS in the cerebrospinal fluid (CSF)) and partially or completely restored integrity of the BBB, e.g., at a time exceeding one week, two weeks, one month, two months, three months, four months, five months, six months, nine months, or one year ("first period"). The rhNaGlu protein can be administered therapeutically or prophylactically, or both. The rhNaGlu can be administered to the subject, alone or in combination with other therapeutic modalities as described herein.

In some embodiments, rhNaGlu is intravenously administered at a first dose periodically for a first period, and intravenously at a second dose periodically for a second period. In one embodiment, there can be a washout period between the first period and the second period that the patient does not receive any rhNaGlu therapy. In one embodiment, the treatment under the first period reduces heparan sulfate (HS) levels (e.g., in the CSF) at least 20%, at least 30%, at least 40%, at least 50%, at least 60%, at least 70%, at least 80% or at least 90% from pretreatment levels. In a preferred embodiment, the treatment under the first period reduces HS levels (e.g., in the CSF) at least 50% from pretreatment levels. In one embodiment, the treatment under the second period is to maintain or further reduce the HS levels (e.g., in the CSF) from those of the first period. In a preferred embodiment, the patient is dosed during the first period more frequently than during the second period. In one embodiment, the amount of rhNaGlu administered per infusion or injection in the first period and the amount of rhNaGlu administered in per infusion or injection in the second period can be the same, but the frequency of administration can be different. For example, the patient can be dosed less frequently during the second period than during the first period. In one embodiment, the amount of the first dose per infusion or injection is higher than the amount of the second dose per infusion or injection. For example, the first dose in the first period is about 0.1 mg/kg body weight, about 0.3 mg/kg body weight, about 0.5 mg/kg body weight, about 1 mg/kg body weight, 3 mg/kg body weight, about 5 mg/kg body weight, about 8 mg/kg body weight, about 10 mg/kg body weight, about 15 mg/kg body weight, about 20 mg/kg body weight, about 25 mg/kg body weight, about 30 mg/kg body weight, about 35 mg/kg body weight, about 40 mg/kg body weight, about 50 mg/kg body weight per infusion or injection. The second dose can be about 0.5 mg/kg body weight, about 1 mg/kg body weight, 3 mg/kg body weight, about 5 mg/kg body weight, about 8 mg/kg body weight, about 10 mg/kg body weight, about 15 mg/kg body weight, about 20 mg/kg body weight, about 25 mg/kg body weight, about 30 mg/kg body weight, about 35 mg/kg body weight, about 40 mg/kg body weight, about 50 mg/kg body weight per infusion or injection. In one embodiment, the first dose is administered one time about 7 days to one time of about 30 days. In one embodiment, the first dose is administered one time about 7 days. In one embodiment, the first dose is administered one time about 10 days. In one embodiment, the first dose is administered one time about 14 days. In one embodiment, the first dose is administered one time about 30 days. In one embodiment, the second dose is administered less frequently than the first dose, for example, one time about 10 days to one time of about 60 days. In one embodiment, the second dose is administered one time about 14 days or one time about 90 days. In a preferred embodiment, the second dose is administered one time about 14 days or one time about 30 days. Optionally, once the CSF HS level is reduced at least, for example, 50%, 60%, 70%, 80% or more from the pretreatment level, the patient may not receive treatment for about 1 month, about 2 months, about 3 months, about 4 months, about 5 months or about 6 months before the second dose initiates.

In one embodiment, the first dose per infusion or injection in the first period can be about 10 mg/kg body weight and the second dose in the second period is about 5 mg/kg body weight. In another embodiment, the first dose per infusion or injection in the first period can be about 10 mg/kg body weight once a week (e.g., once about every 7 days) and the second dose in the second period is about 10 mg/kg body weight twice a month (e.g., once about every 14 days).

The therapeutic methods of the present invention encompass any systemic route of administration which facilitates the uptake or transport of the rhNaGlu protein into the pertinent organs and tissues; as used herein, a systemic route of administration does not include intrathecal delivery or any other method of delivery directly to the CNS. In preferred embodiments, the rhNaGlu protein may be administered to the patient intravenously (e.g., via intravenous injection, intravenous infusion) and crosses even the intact blood brain barrier (BBB) of the subject with NaGlu deficiency.

As discussed above, one of the features of the rhNaGlu proteins as described herein is that they are able to effectively and extensively diffuse across the blood brain barrier (BBB) and brain surface and penetrate various layers or regions of the brain, including deep brain regions, when administered intravenously, and notably, even in mammals with an intact BBB, e.g., normal mammals. The methods of treatment described herein effectively deliver the rhNaGlu proteins to various tissues and neurons or cells of the central nervous system (CNS) in patients with MPS IIIB who are undergoing long-term therapy and have restored BBB integrity. Furthermore, the methods of the present invention deliver sufficient amounts of the rhNaGlu proteins to the blood stream and various peripheral organs and tissues.

rhNaGlu

The methods described herein include the systemic, e.g., intravenous, administration of compositions of rhNaGlu (amino acid sequence 24-743 set forth in SEQ ID NO:1) having patterns of glycosylation that confer an increased cellular uptake and an increased subcellular activity which are particularly useful for therapy, for example, in the treatment of Sanfilippo Syndrome B (mucopolysaccharidosis (MPS) IIIB).

```
Human NaGlu Amino Acid Sequence (signal peptide: aa1-23, underlined)
                                                            (SEQ ID NO: 1)
    MEAVAVAAAV GVLLLAGAGG AAGDEAREAA AVRALVARLL GPGPAADFSV SVERALAAKP    60

GLDTYSLGGG GAARVRVRGS TGVAAAAGLH RYLRDFCGCH VAWSGSQLRL PRPLPAVPGE   120

LTEATPNRYR YYQNVCTQSY SFVWWDWARW EREIDWMALN GINLALAWSG QEAIWQRVYL   180

ALGLTQAEIN EFFTGPAFLA WGRMGNLHTW DGPLPPSWHI KQLYLQHRVL DQMRSFGMTP   240

VLPAFAGHVP EAVTRVFPQV NVTKMGSWGH FNCSYSCSFL LAPEDPIFPI IGSLFLRELI   300
```

```
KEFGTDHIYG ADTFNEMQPP SSEPSYLAAA TTAVYEAMTA VDTEAVWLLQ GWLFQHQPQF    360

WGPAQIRAVL GAVPRGRLLV LDLFAESQPV YTRTASFQGQ PFIWCMLHNF GGNHGLFGAL    420

EAVNGGPEAA RLFPNSTMVG TGMAPEGISQ NEVVYSLMAE LGWRKDPVPD LAAWVTSFAA    480

RRYGVSHPDA GAAWRLLLRS VYNCSGEACR GHNRSPLVRR PSLQMNTSIW YNRSDVFEAW    540

RLLLTSAPSL ATSPAFRYDL LDLTRQAVQE LVSLYYEEAR SAYLSKELAS LLRAGGVLAY    600

ELLPALDEVL ASDSRFLLGS WLEQARAAAV SEAEADFYEQ NSRYQLTLWG PEGNILDYAN    660

KQLAGLVANY YTPRWRLFLE ALVDSVAQGI PFQQHQFDKN VFQLEQAFVL SKQRYPSQPR    720

GDTVDLAKKI FLKYYPRWVA GSW                                           743
```

In some aspects, the composition can be an isolated mixture of rhNaGlu comprising the amino acid sequence 24-743 of SEQ ID NO:1. In some embodiments, the mixture contains a sufficient amount of rhNaGlu having at least one glycan structure that contains phosphorylated mannose (e.g., M6P and bis-M6P) such that the rhNaGlu containing M6P is internalized into a human cell deficient in NaGlu and restores at least 50% of NaGlu activity observed in a wild-type human cell of the same type that actively expresses endogenous NaGlu. In one aspect, at least 10%, 20%, 30%, 40%, 50%, 60%, 70%, 80%, 90%, 91%, 92%, 93% 94%, 95%, 96%, 97%, 98% or 99% of rhNaGlu in the mixture contains at least one glycan structure having phosphorylated mannose. In some embodiments, at least 10% of rhNaGlu in the mixture contains at least one glycan structure having phosphorylated mannose. In some embodiments, at least 20% of rhNaGlu in the mixture contains at least one glycan structure having phosphorylated mannose. In some embodiments, at least 30% of rhNaGlu in the mixture contains at least one glycan structure having phosphorylated mannose. In some embodiments, at least 30% of rhNaGlu in the mixture contains at least one glycan structure having phosphorylated mannose. In some embodiments, at least 40% of rhNaGlu in the mixture contains at least one glycan structure having phosphorylated mannose. In some embodiments, at least 50% of rhNaGlu in the mixture contains at least one glycan structure having phosphorylated mannose. In some embodiments, at least 60% of rhNaGlu in the mixture contains at least one glycan structure having phosphorylated mannose.

In some aspects, the rhNaGlu contains one or more N-linked glycan structure. The rhNaGlu contains at least one phosphorylated mannose (M6P or bis-M6P) which allows the protein to be taken up into a human cell, including but not limited to, a skin fibroblast, an endothelial, a neuronal cell, hepatocyte, a macrophage or any cell that expresses M6P receptor on the cell surface via M6P receptor-mediated endocytosis. In some embodiments, the rhNaGlu contains at least one mannose (Man). In another embodiment, the rhNaGlu contains at least one N-acetylglucosamine (GlcNAc).

In some aspects, the rhNaGlu contains a glycan structure comprising a phosphorylated mannose (M6P or bis-M6P). It is to be understood that M6P referred herein can include mono- and bis-phosphorylated mannose. In some embodiments, the M6P is present at a concentration that is about 0.5, about 1, about 2, about 3, about 4, about 5 or about 6 mole(s) per mole of protein. In some embodiments, the rhNaGlu contains M6P at a concentration that is about 2, about 3, about 4, or about 5 moles per mole of protein. In some embodiments, the rhNaGlu contains M6P at a concentration that is about 2 moles per mole of protein. In some embodiments, the rhNaGlu contains M6P at a concentration that is about 3 moles per mole of protein. In some embodiments, the rhNaGlu contains M6P at a concentration that is about 1 moles per mole of protein. In some embodiments, the rhNaGlu contains M6P at a concentration that is about 2 moles per mole of protein. In some embodiments, the rhNaGlu contains M6P at a concentration that is about 3 moles per mole of protein. In some embodiments, the rhNaGlu contains M6P at a concentration that is about 4 moles per mole of protein. In some embodiments, the rhNaGlu contains M6P at a concentration that is about 5 moles per mole of protein. In some embodiments, the rhNaGlu contains M6P at a concentration that is about 6 moles per mole of protein.

In some aspects, the rhNaGlu contains a sufficient amount of M6P or bis-M6P for cellular uptake into a human cell having a M6P receptor on the cell surface via M6P receptor-mediated endocytosis. In some embodiments, a sufficient amount of M6P or bis-M6P for uptake into a human cell is about 0.5, 1, 2, 3, 4, 5 or 6 moles per mole of protein. The rhNaGlu can be internalized into a human cell deficient in NaGlu such that the internalized protein fully (100% or more) restores a normal level of NaGlu activity in the human cell deficient in NaGlu. In some embodiments, the internalized rhNaGlu protein fully restores a normal level of NaGlu activity in the human cell at a concentration that is at least 0.5, 0.6, 0.7, 0.8, 0.9 or 1.0 µg/mL. In some embodiments, the internalized rhNaGlu fully restores a normal level of NaGlu activity in the human cell deficient in NaGlu at a concentration that is at least 2, 3, 4, 5, 6, 7, 8, 9 or 10 µg/mL. In some embodiments, the internalized rhNaGlu fully restores a normal level of NaGlu activity in the human cell at a concentration that is at least 20, 30, 40, 50, 60, 70, 80, 90 or 100 µg/mL. As used herein, the normal level of NaGlu activity is a level of NaGlu activity measured in a wild-type human cell of the same type that actively expresses a normal NaGlu enzyme.

In some aspects, the rhNaGlu can be internalized into a human cell deficient in NaGlu such that the protein restores at least about 50%, about 60%, about 70%, about 80%, about 90% or about 95% of NaGlu activity of a normal human cell of the same type.

In some embodiments, the rhNaGlu can be internalized into a human cell deficient in NaGlu such that the internalized rhNaGlu provides a higher enzymatic activity than that observed in a normal human cell of the same type.

In some embodiments, the rhNaGlu is internalized into a human cell deficient in NaGlu such that the internalized rhNaGlu provides about 2, about 3, about 4, about 5, about 6, about 7, about 8, about 9 and about 10-fold higher activity than that observed in a normal human cell of the same type. In some embodiments, the rhNaGlu is internalized into a human cell deficient in NaGlu such that the internalized rhNaGlu provides about 15, about 20, about 25, about 30, about 40, about 50, about 60, about 70, about 80, about 90 or about 100-fold higher activity than that observed in a normal human cell.

In some embodiments, the human cell deficient in NaGlu is any human cell deficient in NaGlu that expresses one or more M6P receptors on the cell surface. In some embodiments, the human cell deficient in NaGlu is a human mucopolysaccharidosis (MPS) IIIB fibroblast that accumulates heparan sulfate. In some embodiments, the human cell deficient in NaGlu is a hepatocyte. In some embodiments, the human cell deficient in NaGlu is a neuronal cell, or a glial cell. In some embodiments, the human cell deficient in NaGlu is an endothelial cell. In some embodiments, the human cell deficient in NaGlu is a macrophage.

In some aspects, uptake of rhNaGlu into a human cell is inhibited by the presence of about 1, about 2, about 3, about 4, about 5, about 6, about 7, about 8, about 9 or about 10 mM of competing M6P monosaccharide. In some aspects, the cellular uptake of rhNaGlu is inhibited by the presence of about 0.1, about 0.2, about 0.3, about 0.4, about 0.5, about 0.6, about 0.7, about 0.8, about 0.9 or about 1.0 mM of M6P monosaccharide. In some embodiments, the cellular uptake of rhNaGlu is inhibited by the presence of about 0.01, about 0.02, about 0.03, about 0.04, about 0.05, about 0.06, about 0.07, about 0.08, or about 0.09 mM of M6P monosaccharide.

In some aspects, the rhNaGlu contains mannose in its glycan structures at a concentration that is about 17, 18, 19, 20, 21, 22, 23, 24, 25, 26, 27, 28, 29, 30, 31, 32, 33, 34 or 35 moles per mole of protein. In some embodiments, the rhNaGlu has mannose at a concentration that is about 20, 21, 22, 23, 24, 25, 26, 27, 28, 29 or 30 moles per mole of protein. The rhNaGlu contains mannose at a concentration that is about 22, 23, 24, 25, 26, 27 or 28 moles per mole of protein. The rhNaGlu contains mannose at a concentration that is about 24 moles per mole of protein. The rhNaGlu protein contains mannose at a concentration that is about 25 moles per mole of protein. The rhNaGlu contains mannose at a concentration that is about 26 moles per mole of protein. The rhNaGlu contains mannose at a concentration that is about 27 moles per mole of protein. In some embodiments, the rhNaGlu has mannose at a concentration that is between about 20 and about 30 moles per mole of protein.

In some aspects, the rhNaGlu comprises N-acetylglucosamine (GlcNAc). In some embodiments, the rhNaGlu contains GlcNAc at a concentration that is between about 28 and about 42 moles per mole of protein. In some embodiments, the NaGlu protein has GlcNAc at a concentration that is between about 30 and about 40 moles per mole of protein. In some embodiments, the NaGlu protein comprises GlcNAc at a concentration that is between about 32 and about 38 moles per mole of protein. In some embodiments, the NaGlu protein comprises GlcNAc at a concentration that is between about 34 and about 36 moles per mole of protein. In some embodiments, the NaGlu protein has GlcNAc at a concentration that is about 35 moles per mole of protein. In some embodiments, the rhNaGlu protein contains GlcNAc at a concentration that is about 30, 31, 32, 33, 34, 35, 36, 37, 38, 39 or 40 moles per mole of protein.

In some aspects, the rhNaGlu contains N-acetylgalactosamine (GalNAc) and/or galactose (Gal). The presence of the GalNAc and Gal typically indicates that the NaGlu may contain one or more O-linked glycan structures which are added to the protein in the Golgi compartment. Accordingly, the present invention optionally includes a composition comprising an rhNaGlu that contains one or more O-linked glycan structure.

In some embodiments, the rhNaGlu contains galactose at a concentration that is about 1, 2, 3, 4, 5, 6 or 7 moles per mole of protein. In some embodiments, the rhNaGlu has galactose at a concentration that is about 2, 3, 4, 5 or 6 moles per mole of protein. In some embodiments, the rhNaGlu has galactose at a concentration that is about 3 moles per mole of protein. In some embodiments, the rhNaGlu has galactose at a concentration that is about 4 moles per mole of protein.

In some embodiments, the rhNaGlu comprises at least one GalNAc molecule per mole of protein. In some embodiments, the rhNaGlu comprises GalNAc at a concentration that is about 1 or 2 moles per mole of protein.

In some embodiments, the rhNaGlu contains no fucose. In yet another embodiment, the rhNaGlu contains no glucose. In yet another embodiment, rhNaGlu contains neither fucose nor glucose.

In certain aspects, the rhNaGlu is N-glycosylated at 1, 2, 3, 4, 5, 6, 7, 8, 9, or 10 sites with an N-glycan that comprises a bisecting sugar residue. In one embodiment, the bisecting sugar residue is GlcNAc. In a population of such proteins at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 N-glycans comprising a bisecting sugar, such as a bisecting GlcNAc. In another embodiment, the rhNaGlu further comprises at least 1, 2, 3, 4, 5, 6, 7, 8, 9, or at least 10 N-glycans that are high mannose (such as bi-, tri, or tetrantennary high mannose glycans). In yet another embodiment, in a population of such proteins, at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 N-glycans that is high mannose (such as biantennary, triantennary, or tetraantennary). In certain embodiments, at least 80%, 85%, 90%, 95%, 98%, 99%, or 100% of the N-glycans of any such proteins are not sialylated (i.e., lack neuraminic acid). In certain specific aspects, one, two, three, four, or all terminal sugar residues of the N-glycan with a bisecting GlcNAc are GlcNAc. The N-glycan with a bisecting GlcNAc can, for example, be Structure 12 wherein at least one of the GlcNAc's to the left of the curly bracket (Table A) is attached to the mannose closest to the reducing end (i.e., the end at the right of the structure as shown in Table A) of the glycan.

In certain aspects, the rhNaGlu is N-glycosylated at 1, 2, 3, 4, 5, 6, 7, 8, 9, or 10 sites with a complex-type N-glycan that comprises a bisecting sugar. In one embodiment, the bisecting sugar residue is GlcNAc. In a population of such proteins at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 complex-type N-glycans comprising a bisecting sugar, such as a bisecting GlcNAc. In another embodiment, the rhNaGlu further comprises at least 1, 2, 3, 4, 5, 6, 7, 8, 9, or at least 10 N-glycans that are high mannose (such as bi-, tri, or tetrantennary high mannose glycans). In yet another embodiment, in a population of such proteins at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 N-glycans that is high mannose (such as biantennary, triantennary, or tetraantennary). In certain embodiments, at least 80%, 85%, 90%, 95%, 98%, 99%, or 100% of the N-glycans of any such proteins are not sialylated. In certain specific aspects, one, two, three, four, or all terminal sugar residues of the N-glycan with a bisecting GlcNAc are GlcNAc. The N-glycan with a bisecting GlcNAc can, for example, be Structure 12 wherein at least one of the GlcNAc's to the left of the curly bracket (Table A) is attached to the mannose closest to the reducing end (i.e., the end at the right of the structure as shown in Table A) of the glycan.

In certain aspects, the rhNaGlu is N-glycosylated at 1, 2, 3, 4, 5, 6, 7, 8, 9, or 10 sites with a hybrid-type N-glycan that comprises a bisecting sugar residue. In one embodiment, the bisecting sugar residue is GlcNAc. In a population of such proteins at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 hybrid-type N-glycans comprising a bisecting sugar, such as a bisecting GlcNAc. In another embodiment, the rhNaGlu further comprises at least 1, 2, 3, 4, 5, 6, 7, 8, 9, or at least 10 N-glycans that are high mannose (such as bi-, tri-, or tetrantennary high mannose glycans). In yet another embodiment, in a population of such proteins at least 5%, 10%, 20%, 30%, 40%, 50%, 60%, 70%, 80%, 90%, 95%, 98%, or at least 99%, or 100% of the proteins comprise at least 1, 2, 3, 4, 5, 6, 7, 8, 9, or at least 10 N-glycan that is high mannose (such as biantennary, triantennary, or tetraantennary). In certain embodiments, at least 80%, 85%, 90%, 95%, 98%, 99%, or 100% of the N-glycans of any such proteins are not sialylated. In certain specific aspects, one, two, three, or four terminal sugar residues of the N-glycan with a bisecting GlcNAc are GlcNAc. The N-glycan with a bisecting GlcNAc can, for example, be Structure 12 wherein at least one of the GlcNAc's to the left of the curly bracket (Table A) is attached to the mannose closest to the reducing end (i.e., the end at the right of the structure as shown in Table A) of the glycan.

In certain aspects, the rhNaGlu is capable of binding to Phytohaemagglutinin-E (PHA-E). In certain more specific aspects, at least 5%, 10%, 15%, 20%, 25%, 30%, 35%, 40%, 45%, 50%, 55%, 60%, 65%, 70%, 75%, 80%, 85%, 90%, 95%, or all of the proteins in a population of proteins bind to PHA-E.

In certain aspects, the rhNaGlu is N-glycosylated, wherein at least 25%, 50%, 75%, 80%, 90%, 95%, or at least 98% of the glycosylation structures are complex type structures with terminal GlcNAc.

In certain aspects, the rhNaGlu is N-glycosylated on 1, 2, 3, 4, 5, 6, 7, 8, 9, or 10 N-glycosylation sites, wherein at least 25%, 50%, 75%, 80%, 90%, 95%, 98%, or at least 99%, or 100% of the proteins in a population of proteins comprise complex-type N-glycans. More specifically, the rhNaGlu is N-glycosylated on 1, 2, 3, 4, 5, 6, 7, 8, 9, or 10 N-glycosylation sites, wherein at least 25%, 50%, 75%, 80%, 90%, 95%, 98%, or at least 99%, or 100% of the proteins in a population of proteins comprise complex-type N-glycans and wherein the proteins are not sialylated, or carry at most 1, 2, 3, 4, or 5 sialic acid residues per protein.

In certain aspects, the rhNaGlu is characterized by:
a) low sialic acid (i.e., low neuraminic acid) content (i.e., the protein carries at most 1, 2, 3, 4, or 5 sialic acid residues) or absence of sialic acids; and
b) one or more of the following:
(i) at least 1, 2, 3, 4, 5, 6, 7, 8, 9, or 10 mannose-6-phosphate residues,
(ii) at least 1, 2, 3, 4, 5, 6, 7, 8, 9, or 10 bisecting GlcNAc residues,
(iii) at least 1, 2, 3, 4, 5, 6, 7, 8, 9, or 10 high mannose structures, and
(iv) one or more of Structure 1 to 20 (see Table A).

With respect to a population of proteins, at least 5%, 10%, 20%, 30%, 40%, 50%, 60%, 70%, 80%, 90%, 95%, 98%, or at least 99%, or 100% of the proteins are characterized by:
a) low sialic acid (i.e., low neuraminic acid) content (i.e., the protein carries at most 1, 2, 3, 4, or 5 sialic acid residues) or absence of sialic acids; and
b) one or more of the following:
(i) at least 1, 2, 3, 4, 5, 6, 7, 8, 9, or 10 mannose-6-phosphate residues,
(ii) at least 1, 2, 3, 4, 5, 6, 7, 8, 9, or 10 bisecting GlcNAc residues,
(iii) at least 1, 2, 3, 4, 5, 6, 7, 8, 9, or 10 high mannose structures, and
(iv) one or more of Structure 1 to 20 (see Table A).

In certain aspects, the rhNaGlu is N-glycosylated at one or more N-glycosylation sites. Structures of these N-glycans can be selected from Structures 1 to 20 shown in Table A below.

In certain aspects, the rhNaGlu is N-glycosylated on 1, 2, 3, 4, 5, 6, 7, 8, 9, or 10 N-glycosylation sites, wherein at least 25%, 50%, 75%, 80%, 90%, 95%, 98%, or at least 99%, or 100% of the proteins in a population of proteins comprise one or more N-glycans selected from Structure 1 to Structure 20 (Table A).

In certain aspects, the rhNaGlu is N-glycosylated on 1, 2, 3, 4, 5, 6, 7, 8, 9, or 10 N-glycosylation sites, wherein at least 25%, 50%, 75%, 80%, 90%, 95%, 98%, or at least 99%, or 100% of the proteins in a population of proteins comprise one or more N-glycans selected from Structure 8, Structure 12, Structure 15, Structure 16, and Structure 17 (Table A).

In specific aspects, the rhNaGlu carries one or more of structure 8, 12, 15, 16, and 17 of Table A. In more specific aspects, at least 5%, 10%, 15%, 20%, 25%, 30%, 35%, 40%, 45%, 50%, 55%, 60%, 65%, 70%, 75%, 80%, 85%, 90%, 95%, or all of the N-glycosylation sites of a population of the protein comprise one or more of Structure 8, Structure 12, Structure 15, Structure 16, and Structure 17 of Table A.

In certain aspects, the rhNaGlu carries at most 1, 2, 3, 4, or 5 terminal galactose residues. In more specific aspects, such a protein carries no terminal galactose residue. In certain aspects, a population of such proteins comprises substantially no terminal galactose residues (i.e., less than 2% of proteins contain terminal galactose, less than 1%, less than 0.8%, less than 0.5%, less than 0.2%, or less than 0.1% of proteins in the population of proteins carry terminal galactose). In certain aspects, the glycans in a population of such proteins contain substantially no terminal galactose residues (i.e., less than 2% of the glycans contain terminal galactose, less than 1%, less than 0.8%, less than 0.5%, less than 0.2%, or less than 0.1% of the glycans in a population of such proteins carry terminal galactose).

In some aspects, the rhNaGlu lacks sialic acid (i.e., lacks neuraminic acid; more specifically lacks N-acetylneuraminic acid). In certain aspects, the rhNaGlu comprises mannose-6-phosphate but is not sialylated (i.e., lacks neuraminic acid; more specifically lacks N-acetylneuraminic acid). More specifically, the rhNaGlu comprises at least 1, 2, 3, 4, 5, 6, 7, 8, 9, or at least 10 mannose-6-phosphate residues and at most 1, 2, 3, 4, 5, 6, 7, 8, 9, or at most 10 sialic acid residues. A population of such proteins comprises on average at least 1, 2, 3, 4, 5, 6, 7, 8, 9, or at least 10 mannose-6-phosphate residues per protein molecule and at most 1, 2, 3, 4, 5, 6, 7, 8, 9, or at most 10 sialic acid residues. In specific aspects, a population of such proteins comprises on average between 2 and 4, 2 and 3, or between 3 and 4 mannose-6-phosphate residues and no sialic acid or at most 1 sialic acid residue.

In certain aspects, the rhNaGlu is N-glycosylated and comprises a fragment of SEQ ID NO:1, e.g., a fragment of the sequence of amino acids 24 to 743 of SEQ ID NO:1, wherein the fragment is at least 5, 10, 15, 20, 25, 30, 35, 40, 45, 50, 75, or at least 100 amino acids long. In certain embodiment, the protein also comprises amino acid sequences other than amino acid sequences of SEQ ID NO:1.

In certain aspects, the rhNaGlu is N-glycosylated and comprises an amino acid sequence that is at least 50%, 60%, 70%, 80%, 90%, 95%, 98%, 99%, or 100% identical to a fragment of SEQ ID NO:1, e.g., a fragment of the sequence of amino acids 24 to 743 of SEQ ID NO:1, wherein the fragment is at least 5, 10, 15, 20, 25, 30, 35, 40, 45, 50, 75, or at least 100 amino acids long. In certain embodiments, the protein comprises also amino acid sequences other than amino acid sequences of SEQ ID NO:1.

In certain aspects, the rhNaGlu has a pI of between 5.5 and 7.5, or 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5. In certain aspects, the pI of the protein that is capable of accumulating in the CNS after administration outside the BBB (e.g., by intravenous or intramuscular administration) is 0.1, 0.2, 0.3, 0.4, 0.5, 0.6, 0.7, 0.8, 0.9, or 1 higher than the predicted pI for that protein based solely on amino acid sequence. In certain aspects, the pI of the protein that is capable of accumulating in the CNS after administration outside the BBB (e.g., by intravenous or intramuscular administration) is about the same as the predicted pI for that protein solely based on amino acid sequence.

In certain aspects, the rhNaGlu carries a post-translation modification that facilitates membrane localization such as myristoylation (attachment of myristate), palmitoylation (attachment of palmitate), isoprenylation or prenylation (the addition of an isoprenoid group (e.g. farnesol and geranylgeraniol, i.e., farnesylation, geranylgeranylation); glypiation (glycosylphosphatidylinositol (GPI) anchor formation via an amide bond to C-terminal tail).

In Table A, the residue to the left of the curly brackets can be at any potential position of the structure to the right of the curly brackets. P=phosphate. A legend for the symbols is provided below Table A.

TABLE A

Illustrative N-Glycosylation Structures

| Structure No. | Structure |
|---|---|
| 1 | 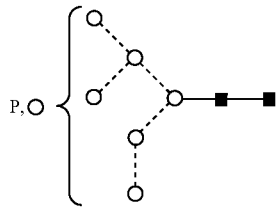 |
| 2 | 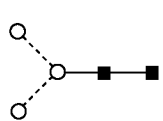 |

TABLE A-continued

Illustrative N-Glycosylation Structures

| Structure No. | Structure |
|---|---|
| 3 | 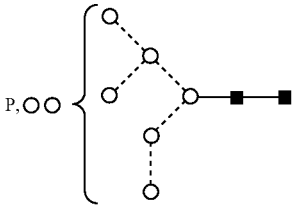 |
| 4 | 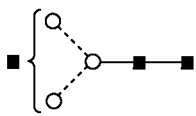 |
| 5 | 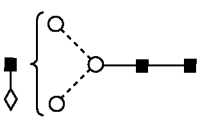 |
| 6 | 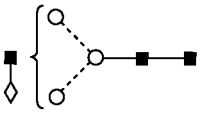 |
| 7 | 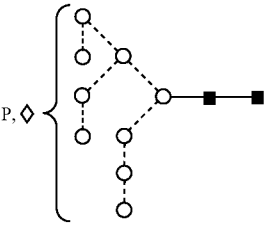 |
| 8 | 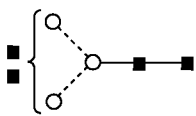 |
| 9 | 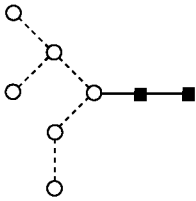 |
| 10 | 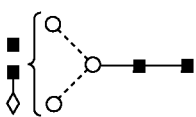 |
| 11 | 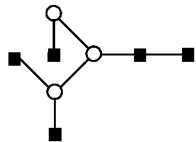 |

TABLE A-continued

Illustrative N-Glycosylation Structures

| Structure No. | Structure |
|---|---|
| 12 | 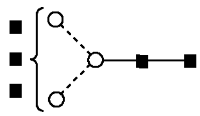 |
| 13 | 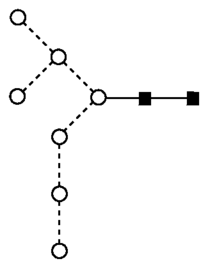 |
| 14 | 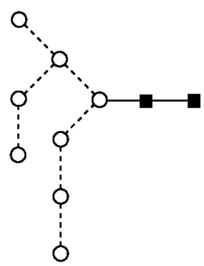 |
| 15 | 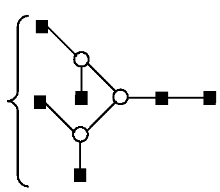 |
| 16 | 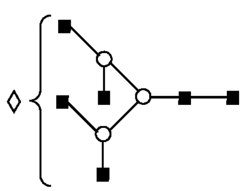 |
| 17 | 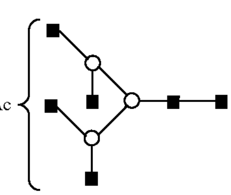 |
| 18 | 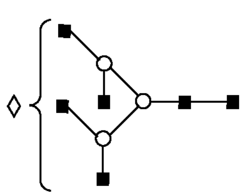 |
| 19 | 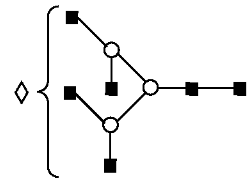 |
| 20 | 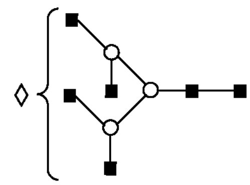 |

Symbols

| Monosaccharide Symbol | Linkage position |
|---|---|
| □ Glc | |
| ■ GlcNAc | |
| ◊ Gal | |
| ◆ GalNAc | |
| ⬨ Fuc (deoxygalactose) | |
| ○ Man | |
| ★ NeuNAc | |
| △ Xylose | |

Linkage type
—— β-linkage
----- α-linkage
∿ unknown linkage

SYMBOLS, ABBREVIATIONS AND LINKAGES [D. J. Harvey et al., Proteomics, 9, (2009), 3796]

The present invention also contemplates compositions of modified rhNaGlu proteins produced from modified nucleic sequences of rhNaGlu. The modified nucleic acid sequences include deletions, insertions, or substitutions of different nucleotides resulting in a polynucleotide that encodes a functionally equivalent polynucleotide or polypeptide. The encoded protein may also contain deletions, insertions, or substitutions of amino acid residues that produce a silent change and result in a functionally equivalent protein or polypeptide. Deliberate amino acid substitutions can be made on the basis of similarity in polarity, charge, solubility, hydrophobicity, hydrophilicity, and/or the amphipathic nature of the residues as long as the biological activity of the NaGlu is retained. For example, negatively charged amino acids can include aspartic acid and glutamic acid; positively charged amino acids can include lysine and arginine; and amino acids with uncharged polar head groups having similar hydrophilicity values can include leucine, isoleucine, and valine; glycine and alanine; asparagine and glutamine; serine and threonine; phenylalanine and tyrosine.

In other aspects, the rhNaGlu can be modified such that it contains an additional moiety or second peptide. In some embodiments, transferrin receptor ligand (TfRL) can be attached to human NaGlu at N- or C-terminus of NaGlu protein. In some embodiments, the transferrin receptor ligand can be attached to the C-terminus of the rhNaGlu protein. In another embodiment, rhNaGlu is fused to insulinlike growth factor receptor (IGF2R) ligand at N- or C-terminus of the NaGlu protein. In yet another embodiment, the NaGlu protein is fused to low density lipoprotein (LDL) receptor ligand at N- or C-terminus of the NaGlu protein.

In some embodiments, the rhNaGlu is produced in a transgenic avian that contains a transgene encoding the NaGlu protein. In some embodiments, the rhNaGlu is produced in an oviduct cell (e.g., a tubular gland cell) of a transgenic avian (e.g., chicken (*Gallus*)). In some embodiments, the rhNaGlu is glycosylated in the oviduct cell (e.g., tubular gland cell) of the transgenic avian. In some embodiments, the rhNaGlu has a glycosylation pattern resulting from the rhNaGlu being produced in an oviduct cell of a transgenic avian. In some embodiments, the rhNaGlu can be isolated and purified from the content of the hard shell eggs laid by the transgenic avian. In some embodiments, the rhNaGlu can be isolated and purified from egg white of the transgenic avian.

The present invention also includes compositions of an isolated mixture of NaGlu proteins, such as a mixture of one or more fragments and full-length rhNaGlu (e.g., 24-743 set forth in SEQ ID NO:1). In some embodiments, a substantial portion of the mixture contains phosphorylated M6P. In some embodiments, at least 10%, 20%, 30%, 40%, 50%, 60%, 70%, 80%, 85%, 90% 95%, 97%, 98% or 99% of the rhNaGlu in the mixture contains M6P. In yet another embodiment, at least 50% of the isolated rhNaGlu in the mixture contains M6P. In yet another embodiment, at least 60% of the isolated rhNaGlu in the mixture contains M6P. In yet another embodiment, at least 70% of the isolated rhNaGlu in the mixture contains M6P. In yet another embodiment, at least 80% of the isolated rhNaGlu in the mixture contains M6P. In yet another embodiment, at least 90% of the isolated rhNaGlu in the mixture contains M6P. In yet another embodiment, at least 95% of the isolated rhNaGlu in the mixture contains M6P. In yet another embodiment, at least 96% of the isolated rhNaGlu in the mixture contains M6P. In yet another embodiment, at least 97% of the isolated rhNaGlu in the mixture contains M6P. In yet another embodiment, at least 98% of the isolated rhNaGlu in the mixture contains M6P. In yet another embodiment, at least 99% of the isolated rhNaGlu in the mixture contains M6P.

Optionally, the rhNaGlu protein produced from an avian or mammalian expression system (e.g., CHO, HEK293, or human skin fibroblast cell-line) can be further modified to achieve a favorable glycosylation pattern (i.e., an increased amount of M6P or bis-M6P) for cellular uptake while retaining the biological activity. Additional terminal M6P or bis-M6P can be introduced to the rhNaGlu by the general methods applied to other hydrolases as described in U.S. Pat. Nos. 6,670,165, 7,138,262, or U.S. Publication No. 2009/0022702, the entire teachings of each of which are incorporated herein by reference. For example, a highly phosphorylated mannopyranosyl oligosaccharide compound can be derivatized with a chemical compound containing a carbonyl-reactive group, followed by oxidizing the rhNaGlu protein to generate carbonyl (aldehyde) group on one glycan structure of the protein, and reacting the oxidized NaGlu protein with the glycan with the derivatized highly phosphorylated mannopyranosyl oligosaccharide compound to form a new compound having a hydrazine bond.

Vectors

Methods which are well-known to those skilled in the art can be used to construct expression vectors containing sequences encoding NaGlu and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., the entire teachings of which are incorporated herein by reference.

A variety of expression vector/host systems can be utilized to express nucleic acid sequences encoding rhNaGlu. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus) or with bacterial expression vectors (e.g., Ti or pBR322 plasmids); or mammalian cell culture systems (e.g., pTT22 vector).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by vertebrate (e.g., avian or mammalian) cells have a signal peptide or secretory leader sequence which is cleaved from the mature protein once export of the growing protein chain across the rough endoplasmic reticulum (ER) has been initiated. Those of ordinary skill in the art are aware that polypeptides produced in the ER by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., the MEAVAVAAAVGVLLLAGAGGAAG (1-23 of SEQ ID NO:1) signal peptide of human NaGlu is used, or a functional derivative of that sequence that retains the ability to direct the secretion of the polypeptide that is operably associated with it. Alternatively, a heterologous signal peptide (e.g., a heterologous mammalian or avian signal peptide), or a functional derivative thereof, may be used. For example, the wild-type leader sequence may be substituted with the leader sequence of, for example, human tissue plasminogen activator (tPA) or mouse β-glucuronidase.

Production of rhNaGlu

The rhNaGlu can be produced using a transgenic avian that contains in the genome a transgene encoding rhNaGlu. In some embodiments, the transgenic avian is a germline transgenic chicken, quail, duck or turkey. In one particularly useful embodiment, the invention is drawn to the production of rhNaGlu which can be produced in the oviduct of a chicken.

Production of rhNaGlu with or without modification in the avian system (e.g., in the avian oviduct) is within the scope of the methods described herein. In some embodiments, the unmodified rhNaGlu comprises the wild-type amino acid sequence (24-743 of SEQ ID NO:1) with a glycosylation structure (i.e., M6P or bis-M6P) that enables efficient uptake by human cells. In another embodiment, the modified protein can be an rhNaGlu fusion protein having a glycosylation pattern (i.e., M6P or bis-M6P) that enables efficient uptake by human cells.

Host Cells

The present invention also contemplates rhNaGlu produced in any useful protein expression system including, without limitation, cell culture (e.g., avian cells, CHO cells, HEK293 cells and COS cells), yeast, bacteria, and plants.

A host cell strain can be chosen for its ability to modulate the expression of the inserted sequences or to process the expressed rhNaGlu in the desired fashion. Such modifications of the polypeptide of rhNaGlu include, without limitation, glycosylation, phosphorylation, or lipidation. Different host cells such as CHO, COS, HeLa, MDCK, HEK293 and W138, which have specific cellular machinery and characteristic mechanisms for such post-translational activities, can be chosen to ensure the correct modification and processing of the fusion protein of the present invention. An avian tumor cell line is also contemplated as a host cell for expressing the polypeptide of the present invention. Examples of a useful avian cell line (e.g., an avian oviduct tumor cell line) are described in U.S. Pat. Publication No. 2009/0253176, the entire teachings of which are incorporated herein by reference.

Pharmaceutical Compositions

The present invention also features pharmaceutical compositions comprising isolated and substantially purified rhNaGlu or a pharmaceutically acceptable salt thereof. The rhNaGlu proteins may be administered using one or more carriers, e.g., as part of a pharmaceutical formulation, or without a carrier. The carrier(s) must be "acceptable" in the sense of being compatible with the other ingredients of the formulation and not deleterious to the recipient thereof. Compositions comprising such carriers, including composite molecules, are formulated by well-known conventional methods (see, for example, Remington's Pharmaceutical Sciences, 14th Ed., Mack Publishing Co., Easton, Pa.), the entire teachings of which are incorporated herein by reference. The carrier may comprise a diluent. In some embodiments, the pharmaceutical carrier can be a liquid and the protein may be in the form of a solution. The pharmaceutical carrier can be wax, fat, or alcohol. In another embodiment, the pharmaceutically acceptable carrier may be a solid in the form of a powder, a lyophilized powder, or a tablet. In some embodiments, the carrier may comprise a liposome or a microcapsule.

In some embodiments, a pharmaceutical composition comprising rhNaGlu protein further comprises a buffer. Exemplary buffers include acetate, phosphate, citrate and glutamate buffers. Exemplary buffers also include lithium citrate, sodium citrate, potassium citrate, calcium citrate, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, and mixtures thereof. In some embodiments, the buffer is trisodium citrate dihydrate. In some embodiments, the buffer is citric acid monohydrate. In some embodiments, a pharmaceutical composition comprises trisodium citrate dehydrate and citric acid monohydrate.

In some embodiments, a pharmaceutical composition comprising rhNaGlu protein further comprises a stabilizer. Exemplary stabilizers include albumin, trehalose, sugars, amino acids, polyols, cyclodextrins, salts such as sodium chloride, magnesium chloride, and calcium chloride, lyoprotectants, and mixtures thereof. In some embodiments, a pharmaceutical composition comprises human serum albumin.

In some embodiments, it is desirable to add a surfactant to the pharmaceutical composition. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Ranges and values intermediate to the above recited ranges and values are also contemplated to be part of the invention.

In some embodiments, suitable pharmaceutical compositions as described herein may further include one or more bulking agents, in particular, for lyophilized formulations. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%). Ranges and values intermediate to the above recited ranges and values are also contemplated to be part of the invention. The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf-life than a liquid solution of the protein.

Pharmaceutical formulations include those suitable for parenteral administration. Preferably, the pharmaceutical formulations as described herein include those suitable for intravenous administration. The formulations can, where appropriate, be conveniently presented in discrete dosage units and can be prepared by any of the methods well known in the art of pharmacy. The methods of producing the pharmaceutical formulations typically include the step of bringing the therapeutic proteins into association with liquid carriers or finely divided solid carriers or both and then, if necessary, shaping the product into the desired formulation.

rhNaGlu proteins as described herein are formulated for IV administration (e.g., by injection, for example bolus injection or continuous infusion) and can be presented in unit dose form in ampoules, pre-filled syringes, small volume infusion or in multi-dose containers with an added preservative. The therapeutic proteins can be injected by, for example, subcutaneous injections, intramuscular injections, and intravenous (IV) infusions or injections.

In preferred embodiments, the rhNaGlu protein is administered intravenously by IV infusion by any useful method. In one example, the rhNaGlu protein can be administered by intravenous infusion through a peripheral line. In another example, the rhNaGlu protein can be administered by intravenous infusion through a peripherally inserted central catheter. In another example, the rhNaGlu protein can be administered by intravenous infusion facilitated by an ambulatory infusion machine attached to a venous vascular access port. In one embodiment of intravenous infusion, the medication is administered over a period of 1 to 8 hours depending on the amount of medication to be infused and the patient's previous infusion-related reaction history, as determined by a physician skilled in the art. In some embodiments, the rhNaGlu protein is administered intravenously by IV injection.

In some embodiments, the therapeutic proteins are administered by infusion, and the infusion can occur over an extended time period, for example, 30 minutes to 10 hours. Thus, the infusion can occur, for example, over a period of about 1 hour, about 2 hours, about 3 hours, about 4 hours, or about 5 hours. The infusion can also occur at various rates. Thus, for example, the infusion rate can be about 1 mL per hour to about 20 mL per hour. In some embodiments, the infusion rate is 5 mL to 10 mL per hour. In some embodiments, the infusion rate is 1, 2, 3, 4, 5, 6, 7, 8, 9, 10, 11, 12, 13, 14, 15, 16, 17, 18, 19 or 20 mL per hour. In some embodiments, the infusion rate is 0.1 to 5 mg/kg/hr. In some embodiments, the infusion rate is about 0.1, about 0.2, about 0.3, about 0.5, about 1.0, about 1.5, about 2.0, or about 3 mg/kg/hr. Ranges and values intermediate to the above recited ranges and values are also contemplated to be part of the invention.

The therapeutic proteins can take such forms as suspensions, solutions, or emulsions in oily or aqueous vehicles, and can contain formulatory agents such as suspending, stabilizing and/or dispersing agents. The rhNaGlu proteins can be in powder form, obtained by aseptic isolation of sterile solid or by lyophilization from solution, for constitution with a suitable vehicle, e.g., sterile, pyrogen-free water, before use.

Biodistribution and Bioavailability

In various embodiments, once delivered to a target tissue, the rhNaGlu as described herein is localized intracellularly. For example, the rhNaGlu as described herein may be localized to axons, lysosomes, mitochondria or vacuoles of a target cell (e.g., neurons such as Purkinje cells). For example, in some embodiments the rhNaGlu as described herein demonstrates translocation dynamics such that the rhNaGlu moves within the perivascular space (e.g., by pulsation-assisted convective mechanisms). In addition, active axonal transport mechanisms relating to the association of the administered protein or enzyme with neurofilaments may also contribute to or otherwise facilitate the distribution of the rhNaGlu proteins as described herein into the deeper tissues of the central nervous system.

In some embodiments, the rhNaGlu as described herein delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, the rhNaGlu as described herein delivered according to the present invention may achieve an enzymatic level or activity that is at least 5%, 10%, 20%, 30%, 40%, 50%, 60%, 70%, 80%, 90%, 91%, 92%, 93%, 94%, 95%, 96%, 97%, 98% or 99% of the normal level or activity of the corresponding NaGlu enzyme in the target tissue. In some embodiments, the rhNaGlu as described herein delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, the rhNaGlu delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 mnol/hr/mg, 300 nmol/hr/mg, 350 nmol/hr/mg, 400 nmol/hr/mg, 450 nmol/hr/mg, 500 nmol/lar/mg, 550 nmol/hr/mg or 600 nmol/hr/mg in a target tissue. Ranges and values intermediate to the above recited ranges and values are also contemplated to be part of the invention.

In some embodiments, inventive methods according to the present invention are particularly useful for targeting the lumbar region. In some embodiments, the rhNaGlu delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 mmol/hr/mg. Ranges and values intermediate to the above recited ranges and values are also contemplated to be part of the invention.

In general, therapeutic agents (e.g., the rhNaGlu) delivered according to the present invention have sufficiently long half time in CSF and target tissues of the brain, spinal cord, and peripheral organs. In some embodiments, the rhNaGlu delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, the rhNaGlu delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art. Ranges and values intermediate to the above recited ranges and values are also contemplated to be part of the invention.

In certain embodiments, the rhNaGlu delivered according to the present invention achieves a concentration of at least 30 μg/mL in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following administration of the pharmaceutical composition to the subject). In certain embodiments, the rhNaGlu delivered according to the present invention achieves a concentration of at least 2 µg/mL, at least 15 µg/mL, at least 1 µg/mL, at least 7 µg/mL, at least 5 µg/mL, at least 2 µg/mL, at least 1 µg/mL or at least 0.5 µg/mL in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following administration of such pharmaceutical compositions to the subject). Ranges and values intermediate to the above recited ranges and values are also contemplated to be part of the invention.

Blood Brain Barrier in Sanfilippo B Syndrome

The term "intact BBB" as used herein means a BBB that does not have impaired integrity, and functions to exclude solutes (e.g., prevent substances with molecular weights greater than ~400 Da from crossing the BBB by free diffusion) in a manner substantially similar to an intact BBB in an age-matched, normal, healthy subject. Methods of assessing BBB integrity are well known in the art (see, e.g., Schliep and Felgenhauer, J Neurol 218, 77-96 (1978); Skoog et al., Neurol. 50:966-971 (1998); Wang et al., J. Magn. Reson. Imaging, 24:695-700 (2006); and Song et al., Neurobiol. Aging, 32:2183-2189 (2011); Bowman et al., Neurology. 68(21): 1809-1814 (2007); Link and Tibbling, Scand J Clin Lab Invest. 37(5):397-401 (1977); Tibbling et al., Scand J Clin Lab Invest. 37(5):385-90 (1977); and Wada, Intern Med. 37(6):509-13 (1998)). For example, BBB integrity can be assessed in MPS IIIB subjects by estimating the ratio of albumin and/or IgG levels in the CSF to levels in the serum. Briefly, blood samples are collected at the same visit as a lumbar puncture and are analyzed with the CSF to quantify albumin and IgG antibody ratios, e.g., using methods known in the art (e.g., as described in Wada, Intern Med. 37(6):509-13 (1998); and Song et al., Neurobiology of Aging 32:2183-2189 (2011)). The CSF/serum albumin Index (also referred to as CSF/serum albumin ratio, CSF/serum AI and CSF-AI) is calculated as follows: CSF/serum albumin Index=(CSF albumin/serum albumin)×1000 (concentrations in mg/L). The CSF/serum albumin Index can be used to assess the integrity of the blood brain barrier in a human subject.

BBB integrity, or the level of BBB impairment can be estimated, e.g., using the CSF/Serum albumin Index (CSF/Serum AI) determined using methods known in the art, e.g., using the criteria of Schliep and Felgenhauer (Schliep and Felgenhauer, J Neurol 218, 77-96 (1978)) as shown in Table B and as described in Christenson et al., Clin. Chem 29/6:1028-1030 (1983) as shown in Table B:

TABLE B

| CSF/serum AI | Level of BBB Impairment |
| --- | --- |
| less than 9 | no significant impairment |
| 9 to 14.3 | slight impairment |
| 14.3-33.3 | moderate impairment |
| 33.3-100 | severe impairment |
| greater than 100 | total breakdown |

Thus the present methods can be used to deliver rhNaGlu to the CNS of patients who have no significant impairment (and CSF/serum AI of 9 or below) or no more than slight impairment (an CSF/serum AI of about 14.3 or below); or no more than moderate BBB impairment (an CSF/serum AI of about 33.3 or below); or no more than severe BBB impairment (an CSF/serum AI of about 100 or below), where in each case the patient is undergoing long-term enzyme replacement therapy for MPS IIIB. As used in this context, "about" allows for a variation of up to ±0.5.

In a study reported by Eeg-Olofsson et al., Acta Paediatr Scand. 1981 March; 70(2):167-70, protein variables reflecting BBB function in CSF and serum were sub-grouped according to age.

TABLE C

| | Age group, years | | | |
| --- | --- | --- | --- | --- |
| | 0.5-5 | 6-15 | 16-20 | 21-30 |
| Number of subjects | 27 | 16 | 20 | 42 |
| CSF/serum albumin Index ($\times 10^3$) | 2.4 ± 0.8 | 3.1 ± 0.9 | 4.1 ± 1.3 | 4.1 ± 1.2 |
| CSF IgG index | 0.42 ± 0.10 | 0.46 ± 0.11 | 0.50 ± 0.07 | 0.47 ± 0.08 |

Results are given as mean±S.D. Shown in the Table C, the CSF/serum AI, reflecting the blood brain barrier function, increases with age. The upper value of the CSF/serum AI (mean+2 S.D.) was 4.0 for patients between 0.5-5 years, 4.9 for patients between 6-15 years (e.g., 7 years), 6.7 for patients between 16-20 years and 6.5 for patients between 21-30 years. Thus, in certain embodiment of the invention, rhNaGlu is delivered by intravenous administration to the CNS of a patient that is between the ages of 0.5-5 years who has a CSF/serum AI of about 4.0 or less; between the ages of 6-15 years who has a CSF/serum AI of about 4.9 (e.g., 5) or less; between the ages of 16-20 years who has a CSF/serum AI of about 6.7 (e.g., 7) or less, or between the ages of 21-30 years who has a CSF/serum AI of about 6.5 (e.g. 7) or less, where, in each case, the patient is undergoing long-term enzyme replacement therapy for MPS IIIB.

In some embodiments, IgG levels are measured in place of albumin; the CSF/serum IgG ratio=CSF IgG (mg/dL)/serum IgG (g/dL). A normal CSF IgG ratio is in the range of 3-8; the present methods can be used to deliver rhNaGlu to the CNS of subjects who have a CSF/serum IgG ratio of less than 10, or less than 8. See, e.g., Mundt and Shanahan, Graff's Textbook of Routine Urinalysis and Body Fluids, Lippincott Williams & Wilkins (2010). Alternatively, a CSF IgG Index is calculated as (CSF IgG/CSF Albumin)/(Serum IgG/Serum Albumin) wherein a normal level is less than about 0.85; the present methods can be used to deliver rhNaGlu to the CNS of subjects who have a CSF IgG Index of less than about 0.9, or less than about 0.85, or less than about 0.7, or less than about 0.6, or less than about 0.5. As also shown in Table C, the upper value of the CSF IgG Index (mean+2 S.D.) was 0.62 for patients between 0.5-5 years, 0.68 for patients between 6-15 year, 0.64 for patients between 16-20 years and 0.63 for patients between 21-30 years. Thus, in certain embodiments of the invention, rhNaGlu is delivered by intravenous administration to the CNS of a patient that is between the ages of 0.5-30 years, for example, 0.5-5 years, 6-15 years (e.g., about 7 years), 16-20 years and 21-30 years, who has a CSF IgG Index of about 0.7 or less, for example, less than about 1.0 and less than about 0.5, where, in each case, the patient is undergoing long-term enzyme replacement therapy for MPS IIIB.

In some embodiments, the subject has at least 80% of the BBB integrity of a normal healthy subject, e.g., at least 85%, 90%, 95%, or higher, as measured by CSF/serum IgG Index, CSF IgG Index or CSF/serum albumin Index. Exemplary normal values can be determined using methods known in the art, e.g., and can include those set out in Eeg-Olofsson et al., Acta Paediatr Scand. 1981 March; 70(2):167-70.

Alternatively or in addition, BBB integrity can be assessed in MPS IIIB subjects more directly, e.g., using a non-invasive imaging modality. For example, BBB integrity by determining the BBB transfer coefficient ($K^{trans}$), which can be estimated in the MPS IIIB subjects using dynamic contrast-enhanced MR imaging (DCE-MRI), e.g., using methods known in the art (see, e.g., Nagaraja et al., Methods Mol Biol. 686:193-212 (2011); Haris et al., J Magn Reson Imaging. 28(3):588-97 (2008); Park et al., J Control Release. 162(1):134-42 2012); Song et al., Neurobiology of Aging 32:2183-2189 (2011)). In preferred embodiments, a standard contrast agent (e.g., a gadolinium-based contrast agent such as Gadolinium-diethylenetriaminepentaacetic acid (Gd-DTPA) or gadobutrol) is used. BBB permeability, reflected by the rate of transfer of the contrast agent from the blood to brain tissues (referred to herein as $K^{trans}$), is calculated from MR images, e.g., T1-weighted images, e.g., based on the standard model of Tofts et al., J. Magn. Reson. Imaging 10:223-232 (1999); the extended Tofts model (ETM), see Sourbron and Buckley, Magnetic Resonance in Medicine, 66(3):735-745 (2011), Tofts et al., Journal of Magnetic Resonance Imaging, 7(1):91-101 (1997), and Buckley, Magnetic Resonance in Medicine, 47(3):601-606 (2002); or the Patlak algorithm (Patlak et al., Journal of Cerebral Blood Flow and Metabolism, 3(1):1-7 (1983); Nagaraja et al., Methods Mol Biol. 686:193-212 (2011)). See also Bergamino et al. ISRN Neuroscience Volume 2013 (2013), Article ID 905279, 6 pages (available at dx.doi.org/10.1155/2013/905279); Sourbron et al., Magnetic Resonance in Medicine, 62(1):205-217 (2009). Other methods can also be used to determine $K^{trans}$, e.g., magnetization transfer MRI (MT-MRI) based methods that include evaluation of changes in $T_1$ and $T_{1sat}$, see, e.g., Nagaraja et al., Methods Mol Biol. 686:193-212 (2011). A particularly preferred method is the standard Tofts model. As one of skill in the art will appreciate, the threshold value of $K^{trans}$, below which a subject can be considered to have BBB integrity, will vary depending on the imaging method, used the analysis method used, and the contrast agent used. Thus, in the present methods a value for $K^{trans}$ determined in a subject should be compared to a reference value determined using the same imaging methods, analysis method, and contrast agent. One of skill in the art would readily be able to determine such a reference value. Suitable reference values can include a single cut-off (threshold) value, such as a median or mean, or a level that defines the boundaries of an upper or lower quartile, tertile, or other segment of a clinical trial population that is determined to be statistically different with respect to $K^{trans}$ from the other segments. It can be a range of cut-off (or threshold) values, such as a confidence interval. It can be established based upon comparative groups, such as where $K^{trans}$ in one defined group is a fold higher, or lower, (e.g., approximately 2-fold, 4-fold, 8-fold, 16-fold or more) than $K^{trans}$ in another defined group. It can be a range, for example, where a population of subjects (e.g., control subjects) is divided equally (or unequally) into groups, such as a low-$K^{trans}$ group, a medium-$K^{trans}$ group and a high-$K^{trans}$ group, or into quartiles, the lowest quartile being subjects with the lowest $K^{trans}$ and the highest quartile being subjects with the highest $K^{trans}$, or into n-quantiles (i.e., n regularly spaced intervals) the lowest of the n-quantiles being subjects with the lowest $K^{trans}$ and the highest of the n-quantiles being subjects with the highest $K^{trans}$.

In some embodiments, where the methods described in Song et al., supra, are used, a $K^{trans}$ below 0.1/$min^{-1}$ may be used as a reference value.

The methods described herein result in a decrease in the levels of GAG/heparan sulfate in the CSF of the subjects, e.g., a decrease that is sufficient to treat the subject.

In some embodiments, treatment refers to partial or complete alleviation, amelioration, relief, inhibition, delaying onset, reducing severity and/or incidence of neurological impairment in a Sanfilippo B patient. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

Thus, in some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is determined by LAMP-1 staining. Ranges and values intermediate to the above recited ranges and values are also contemplated to be part of the invention.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control. Ranges and values intermediate to the above recited ranges and values are also contemplated to be part of the invention.

In some embodiments, treatment refers to increased NaGlu enzyme activity in various tissues. In some embodiments, treatment refers to increased NaGlu enzyme activity in brain target tissues, spinal cord neurons and/or peripheral target tissues. In some embodiments, NaGlu enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, NaGlu enzyme activity is increased by at least 1-fold, 2-fold, 3-fold, 4-fold, 5-fold, 6-fold, 7-fold, 8-fold, 9-fold or 10-fold as compared to a control. In some embodiments, increased NaGlu enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, NaGlu enzymatic activity is increased in the lumbar region. In some embodiments, increased NaGlu enzymatic activity in the lumbar region is at least approximately 2,000 nmol/hr/mg, 3,000 nmol/hr/mg, 4,000 nmol/hr/mg, 5,000 nmol/hr/mg, 6,000 nmol/hr/mg, 7,000 nmol/ hr/mg, 8,000 nmol/hr/mg, 9,000 nmol/hr/mg, 10,000 nmol/hr/mg, or more. Ranges and values intermediate to the above recited ranges and values are also contemplated to be part of the invention.

In certain embodiments, treatment according to the present invention results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological or biological markers which are associated with the NaGlu associated disease. Such reduction or elimination may be particularly evident in the cells, fluids and tissues of the CNS (e.g., CSF, neurons and oligodendrocytes). For example, in some embodiments, upon administration to a subject, the pharmaceutical compositions of the present invention demonstrate or achieve a reduction in the accumulation of the biomarkers hepatocyte growth factor (HGF) in the subject's CSF or lysosomal associated membrane protein 1 (LAMP 1) in the CNS cells and tissues of the subject (e.g., in the cerebral cortex, cerebellum, caudate nucleus and putamen, white matter and/or thalamus). LAMP1 is a glycoprotein highly expressed in lysosomal membranes and its presence is elevated many patients with a lysosomal storage disorder (Meikle et al., Clin. Chem. (1997) 43:1325-1335). The presence or absence of LAMP 1 in patients (e.g., as determined by LAMP staining) with a lysosomal storage disease therefore may provide a useful indicator of lysosomal activity and a marker for both the diagnosis and monitoring of lysosomal storage diseases.

Accordingly, some embodiments of the present invention relate to methods of reducing or otherwise eliminating the presence or accumulation of one or more pathological or biological markers associated with the NaGlu associated disease (e.g., HGF). Similarly, some embodiments of the invention relate to methods of increasing the degradation (or the rate of degradation) of one or more pathological or biological markers (e.g., LAMP1 and HGF) associated with lysosomal storage diseases. In further embodiments, the invention provides methods for treating the central nervous system (CNS) in a human patient with mucopolysaccharidosis (MPS) IIIB undergoing long-term enzyme replacement therapy with rhNaGlu, the method comprising intravenously administering to said patient a therapeutically effective amount of rhNaGlu to suppress or prevent reaccumulation of HGF levels in CSF, wherein said patient has an intact BBB, and wherein the intravenous administration prevents reaccumulation of HGF levels in the CSF.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. Ranges and values intermediate to the above recited ranges and values are also contemplated to be part of the invention.

In some embodiments, treatment refers to increased survival (e.g., survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer. Ranges and values intermediate to the above recited ranges and values are also contemplated to be part of the invention.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Sanfilippo B, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Sanfilippo B or having the potential to develop Sanfilippo B. The individual can have residual endogenous NaGlu expression and/or activity, or no measurable activity. For example, the individual having Sanfilippo B may have NaGlu expression levels that are less than about 30-50%, less than about 25-30%, less than about 20-25%, less than about 15-20%, less than about 10-15%, less than about 5-10%, less than about 0.1-5% of normal NaGlu expression levels. Ranges and values intermediate to the above recited ranges and values are also contemplated to be part of the invention.

In some embodiments, the individual is an individual who has been recently diagnosed with the disease. Typically, early treatment (treatment commencing as soon as possible after diagnosis) is important to minimize the effects of the disease and to maximize the benefits of treatment.

Combination Therapies rhNaGlu proteins, for instance a rhNaGlu protein containing a sufficient amount of oligosaccharides (e.g., mannose and phosphorylated mannose (i.e., M6P)), can be used alone or in combination to treat NaGlu associated diseases (e.g., Sanfilippo Syndrome B). It should be understood that the rhNaGlu proteins of the invention can be used alone or in combination with an additional procedure, e.g., surgical procedure, or agent, e.g., therapeutic agent, the additional procedure or agent being selected by the skilled artisan for its intended purpose. For instance, the additional procedure or agent can be a therapeutic procedure or agent art-recognized as being useful to treat the disease or condition being treated by the rhNaGlu protein of the present invention. The additional procedure or agent also can be an agent that imparts a beneficial attribute to the therapeutic composition, e.g., an agent which affects the viscosity of the composition.

It should also be understood that the combinations which are included within this invention are those combinations useful for their intended purpose. The agents and procedures set forth below are for illustrative purposes and not intended to be limiting to the present invention. The combinations, which are part of this invention, can be the rhNaGlu proteins of the present invention and at least one additional agent or procedure selected from the lists below. The combination can also include more than one additional agent or procedure, e.g., two or three additional agents if the combination is such that the formed composition can perform its intended function.

The combination therapy can include surgical procedures, gene therapy, or enzyme-replacement therapy. Additionally, the rhNaGlu protein can be coformulated with one or more additional therapeutic agents, e.g., other recombinant proteins or antibodies or drugs capable of preventing or reducing the accumulation of undegraded substrates (e.g., substrate reduction therapy).

In one or more embodiments, the combination therapy can include co-administration with immunosuppressants, as discussed in further detail below. Immunosuppressants such as, but not limited to, antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept), anti-OX-40L antibodies can also be administered before, during, or after administration of a recombinant human protein, such as a rhNaGlu protein, for example, if an anaphylactic reaction or adverse immune response is expected or experienced by a patient.

Immunogenicity

The pharmaceutical compositions of the present invention are characterized by their tolerability. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Generally, administration of an rhNaGlu protein according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

However, in some embodiments, a subject mounts an immune response after being administered the rhNaGlu as described herein. Thus, in some embodiments, it may be useful to render the subject receiving the rhNaGlu as described herein tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly IV infusions of low doses of rhNaGlu may be used.

Any immunosuppressant agent known to the skilled artisan may be employed together with a combination therapy as described herein. Such immunosuppressant agents include but are not limited to cyclosporine, FK506, rapamycin, CTLA4-Ig, and anti-TNF agents such as etanercept (see e.g., Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 2000, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The antiIL2 receptor (α-subunit) antibody daclizumab (e.g., Zenapax™), which has been demonstrated effective in transplant patients, can also be used as an immunosuppressant agent (see e.g., Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1 137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

In other embodiments, the invention includes methods comprising co-administration of the NaGlu proteins of the present invention with agents which decrease or suppress an immune response to the NaGlu protein, e.g., immunosuppressants. Immunosuppressants such as, but not limited to, antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept), anti-OX-40L antibodies can also be administered before, during, or after administration of a recombinant human protein, such as a rhNaGlu protein, for example, if an anaphylactic reaction or adverse immune response is expected or experienced by a patient.

In some embodiments, the invention provides for a pre-treatment procedure to minimize or prevent any potential anaphylactic reactions that can be incurred by administration of the recombinant protein in accordance with the invention. In some embodiments, to prevent a potential anaphylactic reaction, an H-1 receptor antagonist, also known as an antihistamine (e.g., diphenhydramine) is administered to the patient. In some embodiments, the H-1 receptor antagonist is administered in a dose of about 1 mg to about 10 mg per kilogram of body weight. For example, an antihistamine can be administered in a dose of about 5 mg per kilogram. In some embodiments, the antihistamine is administered in a dose of between about 0.1 mg and about 10 mg per kilogram of body weight. In some embodiments, the antihistamine is administered in a dose between about 1 mg and about 5 mg per kilogram of body weight. For example the dose can be 1 mg, 2 mg, 3 mg, 4 mg, or 5 mg per kilogram of body weight. The antihistamine can be administered by any useful method. In some embodiments, the antihistamine is administered intravenously. In another embodiment, the antihistamine is administered in pharmaceutically acceptable capsules.

Administration of the antihistamine can be prior to the administration of the recombinant NaGlu in accordance with the invention. In some embodiments, the H-1 receptor antagonist is administered about 10 to about 90 minutes, for example, about 30 to about 60 minutes prior to the administration of recombinant NaGlu. The H-1 receptor antagonist can be administered using an ambulatory system connected to a vascular access port. In some embodiments, the antihistamine is administered about 90 minutes prior to the administration of recombinant NaGlu. In some embodiments, the antihistamine is administered between about 10 and about 60 minutes prior to the administration of recombinant NaGlu. In another embodiment, the antihistamine is administered between about 20 and about 40 minutes prior to administering recombinant NaGlu. For example, the antihistamine can be administered 20, 25, 30, 35, or 40 minutes prior to the administration of recombinant NaGlu.

In some embodiments, the antihistamine administered is diphenhydramine. Any useful antihistamine can be used. Such antihistamines include, without limitation, clemastine, doxylamine, loratidine, desloratadine, fexofenadine, pheniramine, cetirizine, ebastine, promethazine, chlorpheniramine, levocetirizine, olopadatine, quetiapine, meclizine, dimenhydrinate, embramine, dimethindene, and dexchlorpheniramine.

In another embodiment, with reference to intravenous infusion, the potential for anaphylactic reactions can be reduced by administering the infusions using a ramp-up protocol. In this context, a ramp-up protocol refers to slowly increasing the rate of the infusion over the course of the infusion in order to desensitize the patient to the infusion of the medication.

Kits

The present invention further provides kits or other articles of manufacture which contain the rhNaGlu of the present invention and provide instructions for its reconstitution (if lyophilized) and/or use. Kits or other articles of manufacture may include a container, a catheter and any other articles, devices or equipment useful in IV administration. Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, a label on, or associated with, the container may indicate directions for use and/or reconstitution. For example, the label may indicate that the formulation is reconstituted to protein concentrations as described above. The label may further indicate that the formulation is useful or intended for intravenous administration. In some embodiments, a container may contain a single dose of a stable formulation containing a replacement enzyme (e.g., an rhNaGlu protein). In various embodiments, a single dose of the stable formulation is present in a volume of less than about 15 mL, 10 mL, 5.0 mL, 4.0 mL, 3.5 mL, 3.0 mL, 2.5 mL, 2.0 mL, 1.5 mL, 1.0 mL, or 0.5 mL. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/mL (e.g., at least 5 mg/mL, at least 10 mg/mL, at least 25 mg/mL, at least 50 mg/mL, at least 75 mg/mL, at least 100 mg/mL).

Kits or other articles of manufacture may further include other materials desirable from a commercial and user standpoint, including other buffers, diluents, filters, needles, catheters, syringes, and package inserts with instructions for use. Ranges and values intermediate to the above recited ranges and values are also contemplated to be part of the invention.

EXAMPLES

The invention is further described in the following examples, which do not limit the scope of the invention described in the claims.

Example 1. Investigation of the Pharmacokinetics of $^{89}$Zr Labeled rhNaGlu in Normal Rats This Example describes the results of $^{89}$Zr labeling of rhNaGlu and investigation of the pharmacokinetics of $^{89}$Zr Labeled rhNaGlu in normal rats (wild-type) at 1 and 10 mg/kg (with additional data points at 0.3 and 20 mg/kg).

The animals (males and females, ca. 200 g) were anesthetized with sodium pentobarbital (35-50 mg/kg intraperitoneal, with supporting additional doses as needed). Heparinized IV catheters were installed in one of the tail veins and flushed with sterile saline. rhNaGlu was administered through the IV catheter as a fast (10 seconds) bolus. 2 hours after administration of $^{89}$Zr-labeled rhNaGlu, the animals were then euthanized with an overdose of pentobarbital (100 mg/kg) and dissected. The radioactivity of tissue samples was measured in a high energy automatic well counter. Values for the four animals (2 male and 2 female at 1 or 10 mg/kg each) are shown in Table D. Liver was again the critical organ with respect to the absorbed dose. Although the levels of rhNaGlu in the brain and spinal cord were relatively low compared to other organs, the levels were clinically significant as a relatively low amount of enzyme is required for treating the central nervous system.

TABLE D

|  | Brain | Spinal cord | Liver |
| --- | --- | --- | --- |
| 10 mg/kg Female | 0.00304387% | 0.24186145% | 4.33381816% |
| 1 mg/kg Female | 0.00287837% | 0.05088844% | 4.02076250% |
| 10 mg/kg Male | 0.00267734% | 0.08438254% | 4.40880350% |
| 1 mg/kg Male | 0.00033657% | 0.00000000% | 4.03690328% |

Example 2. CNS Penetration of rhNaGlu in Non-Human Primates

This Example describes an investigation of the CNS penetration of rhNaGlu in non-human primates.

rhNaGlu was administered to a normal *M. fascicularis* by intrathecal injection at doses of 3 and 30 mg/kg/dose on Days 1 and 8, followed by intravenous infusion at 3 or 30 mg/kg/dose on Days 15 and 22. This dose was well tolerated in the monkeys. Enzyme levels were measured over the following 9 hours. As shown in FIG. 1, an increase in rhNaGlu concentration was seen in the CSF on both Days 15 and 22, demonstrating CNS penetration of the IV-administered rhNaGlu.

Figure 2:
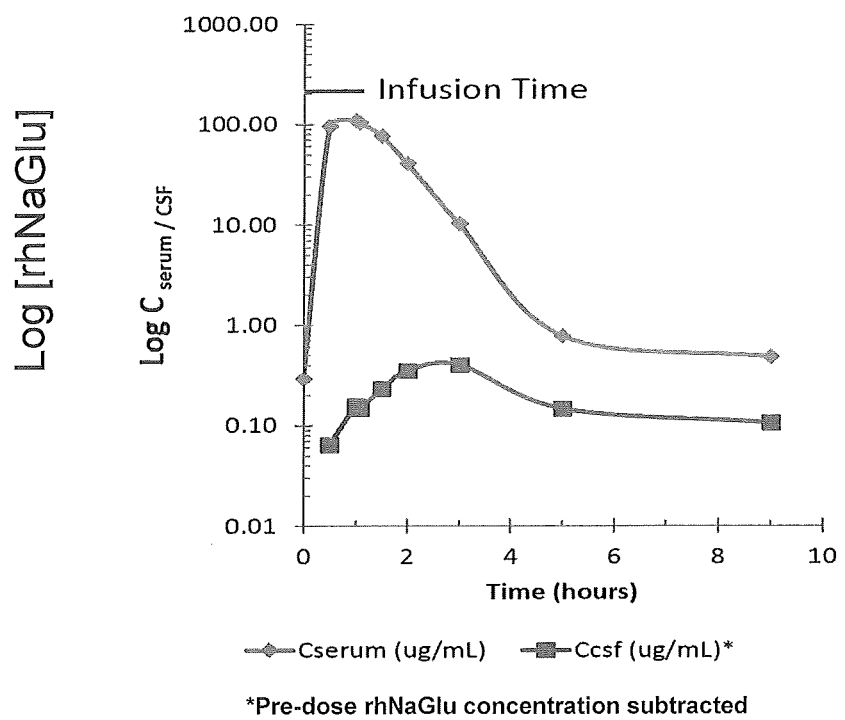
FIG. 2 shows a semi-log plot of rhNaGlu levels in serum (diamonds) or CSF (squares) following a single 1 hour IV infusion at 30 mg/kg/dose monitored over 9 hours. Each time point represents the average of 6 samples tested: 3 animals×2 weekly doses. Pre-dose rhNaGlu concentrations were subtracted from each CSF time point before plotting on graph.

In additional experiments, a single 1 hour IV infusion was given at 30 mg/kg/dose followed by measuring enzyme activity over the next 9 hours. 6 samples were tested at each time point: 3 animals×2 weekly doses. The concentration of rhNaGlu in the CSF following IV infusion shown in FIG. 2 demonstrates CNS penetration of the IV-administered rhNaGlu.

Example 3. Assessing Blood Brain Barrier (BBB) Integrity in Human Patients with MPS IIIB 3.1 This example explores the integrity of the BBB of MPS IIIB subjects using two complimentary and widely accepted methodologies, the CSF/serum albumin index (CSF-AI) and dynamic contrast-enhanced magnetic resonance imaging (DCEMRI).

Subjects over 5 years of age with a definitive diagnosis of MPS IIIB, as determined by either a documented deficiency in alpha-N-acetylglucosaminidase (NaGlu) enzyme activity or documented functionally-relevant mutations in both alleles of the NaGlu gene.

The example includes assessing BBB integrity in the MPS IIIB subjects undergoing enzyme replacement therapy by estimating the ratios of albumin or IgG proteins present in the CSF versus the serum. Briefly, blood samples are collected at the same visit as a lumbar puncture and are analyzed with the CSF to quantify albumin and IgG antibody ratios using methods known in the art. The CSF/serum albumin Index is calculated as follows: CSF/serum albumin Index=(CSF albumin/serum albumin)×1000 (concentrations in mg/L). The CSF/serum albumin Index is used to assess the integrity of the blood brain barrier in a human subject with MPS IIIB undergoing enzyme replacement therapy. Alternatively, the CSF-IgG Index is calculated, in a similar manner.

The BBB transfer coefficient ($K^{trans}$) is estimated in the MPS IIIB subjects using dynamic contrast-enhanced MR imaging (DCE-MRI), e.g., using methods known in the art (see, e.g., Song et al., Neurobiology of Aging 32:2183-2189 (2011)). A standard contrast agent or a labeled rhNaGlu, e.g., 89Zr-labeled rhNaGlu is used. $K^{trans}$ is calculated from MR images, e.g., T1-weighted images, based on the two-compartment model of Tofts et al., J. Magn. Reson. Imaging 10:223-232 (1999)). ROIs are placed manually in, e.g., the basal ganglia and periventricular white matter. See, e.g., Song et al., supra.

3.2 BBB integrity and structural brain abnormalities were evaluated in MPS IIIB patients using CSF-AI and multimodal MRI. Five Caucasian MPS IIIB patients (4 males, 1 female) with classic severe phenotype between 6 and 8 years of age were enrolled. Their mean age at the time of diagnosis of MPS IIIB was 2.4 years. A blood sample and CSF sample (by lumbar puncture) were obtained for determination of CSF-AI. DCE-MRI (Dynamic Contrast Enhanced-MR') images were obtained before, during, and after intravenous injection of gadoterate meglumine (Dotarem®) contrast agent for determination of blood plasma volume, BBB transfer coefficient ($K^{trans}$, reflecting BBB permeability) and the tissue MRI relaxation time, $T_1$ (reflecting tissue physical properties). Exploratory biomarkers such as HS (in serum, urine, and CSF) and hepatocyte growth factor (HGF) levels in CSF were also evaluated in these patients. CSF-AI ranged between 5.5 to 11.3 in 4 out of 5 patients (upper limit of normal 4.9) with CSF-AI for the fifth patient below the upper limit of normal. DCE-MRI results showed $K^{trans}$ values in grey and white matter that were very low and similar to those previously reported in adult healthy brain, and $T_1$ values in white matter that were comparable to normal volunteers of similar age. Other key findings from the MRI included cerebral atrophy, increased skull thickness and abnormal areas of white matter hyperintensity. Exploratory biomarkers showed substantial increase in HS levels in CSF, serum and urine, and an increase in HGF in CSF (compared to normal range). In MPS IIIB patients, there is evidence of mild BBB leakage based on the CSF-AI findings; these findings are reflected in the absence of clear evidence for BBB leakage on MRI. MRI volumetric measurements were robust and successfully showed evidence for global and tissue-specific atrophy in these patients.

Example 4. Recombinant Human Alpha-N-Acetylglucosaminidase Demonstrates Mannose-6-Phosphate Receptor Dependent Transport in an In Vitro Blood Brain Barrier Model To further investigate potential mechanisms for CNS uptake of recombinant human NaGlu, an in vitro Blood Brain Barrier (BBB) assay was used to monitor rhNaGlu transport across a cell bi-layer composed of primary rat brain capillary endothelial cells on the apical side (representing the blood) with pericytes attached to the opposite side of the filter (basolateral side).

Materials and Methods

Human NaGlu-deficient fibroblasts (GM00156) were purchased from the Coriell Institute (Camden, N.J.). CHO-derived rhNaGlu (CHO-NaGlu) was purchased from R&D Systems (Minneapolis, Minn.).

Figure 3A:
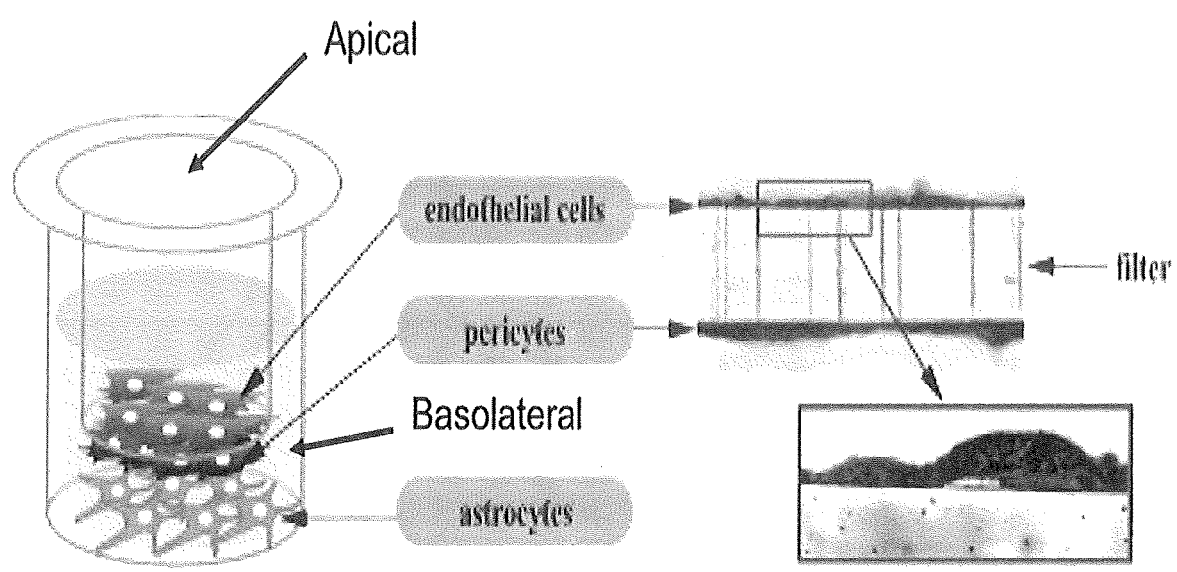
FIG. 3A shows a schematic of the BBB assay cell system. The insert well is placed within the larger lower well. A porous filter separates the medium in the insert well from the medium in the lower well. Endothelial cells are grown on the filter facing the insert well medium while pericytes are grown on the opposite side of the filter facing the lower well medium. Astrocytes are grown on the bottom of the lower well.

Recombinant human NaGlu isolated and purified from egg white of a transgenic avian (EW-NaGlu) was subjected to a rat in vitro BBB assay to monitor its ability to be transported across a cell bi-layer using a commercial BBB kit purchased from PharmaCo-Cell Company Ltd. The bi-layer was composed of primary brain capillary endothelial cells sitting on the apical (blood) side of a porous filter at the bottom of an insert well (FIG. 3A). The filter separated the apical medium from medium contained within the lower well, the basolateral (brain) side. Pericytes were sitting on the opposite side of the filter and were exposed to basolateral medium, and astrocytes are grown on the bottom of the lower well. Brain endothelial cells lose their phenotype when grown in culture without the cross talk of their usual in vivo neighboring cells (primarily pericytes and astrocytes). In this BBB system, both the pericytes and astrocytes provided the necessary factors that allowed the endothelial cells to form tight junctions, a fundamental characteristic of the BBB. Tight junction formation was confirmed for each well used in the assay by measuring the transendothelial electrical resistance (TEER) across the bi-layer using a specialized Ohmmeter. TEER values were measured daily starting on day 2 after putting the cells into culture at 37° C.

Figure 3B:
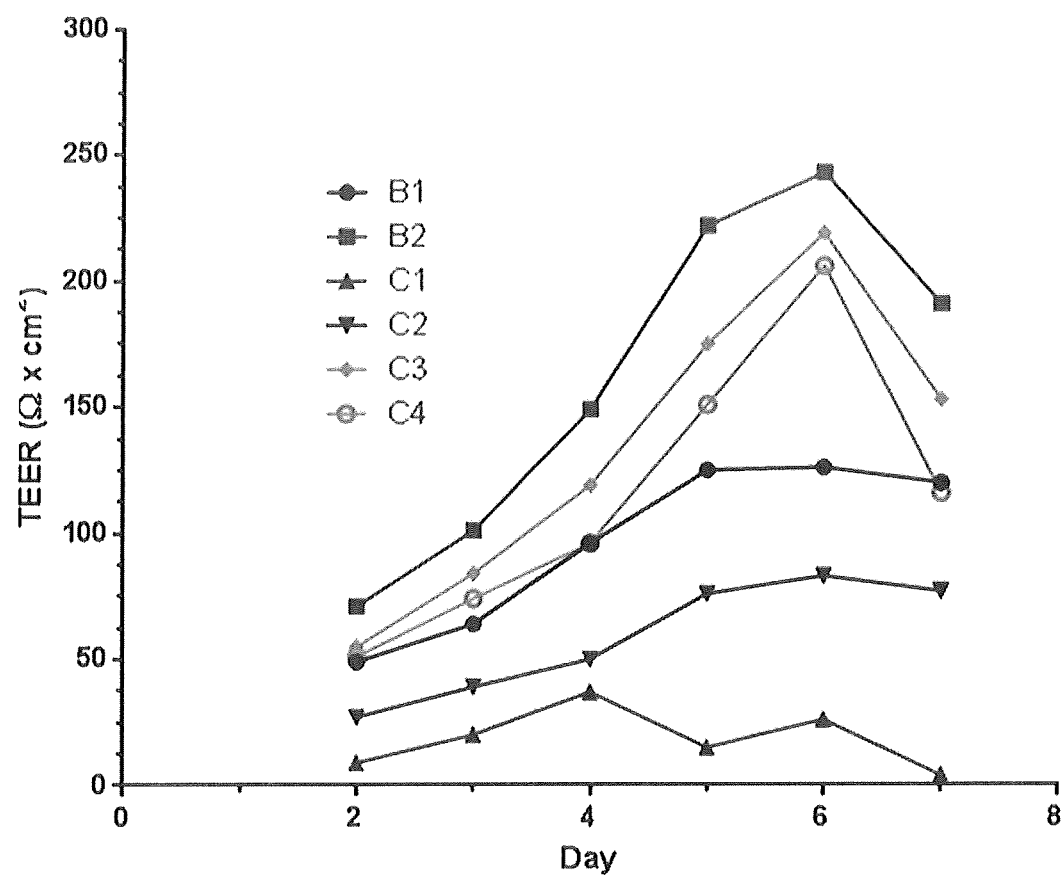
FIG. 3B shows transendothelial electrical resistance (TEER) changes over time in culture in the system shown in FIG. 3A. Once the TEER value of a well reaches $150\Omega \times cm^2$, the well is used in the EW-NaGlu BBB transport experiments. TEER normally reaches this value around day 4 or 5 but begins to drop-off on day 7. Day 7 cells are not used in the study.

(FIG. 3B). These values had to be 150Ω×cm² or greater before the well was used to evaluate the ability of EW-NaGlu to be transported across the bi-layer from the apical side to the basolateral side. Wells that did not achieve this TEER value were not used. At the end of each time course, FITC-labeled dextran was added to each apical well and the amount of fluorescence in the basolateral medium is measured. If tight junctions remained intact, fluorescence attributed to FITC-labeled dextran should not be present in the basolateral medium (Table E). Any well with detectable fluorescence was excluded from the study.

TABLE E

FITC-labeled dextran levels following completion of the BBB cell culture assay

| | Well Number | | | | | | | | | | | |
|---|---|---|---|---|---|---|---|---|---|---|---|---|
| | B1 | B2 | C1 | C2 | C3 | C4 | B3 | B4 | B5 | B6 | C5 | C6 |
| Detectable FITC-labeled Dextran | +++ | − | +++ | ++ | − | − | +/− | ++++ | − | − | − | − |

Wells with a TEER value lower than 150 or with detectable FITC-labeled Dextran were excluded from evaluation Mannose-6-Phosphate (M6P) composition analysis of EW-NaGlu was performed using a 2-Aminobenzoic acid (2-AA) fluorescence-based method. M6P was released from the protein glycans by hydrolysis using 6.7 M trifluoroacetic acid at 100° C. for 3 hours. The samples were then dried and labeled with 2-Aminobenzoic acid. The labeled M6P was analyzed by normal phase HPLC on a hydrophilic/anion exchange mixed mode column using an ammonium formate/acetonitrile mobile phase at pH 4.4. Fluorescence detection excitation and emission wavelengths were 360 and 425 nm. Quantitation was performed using a M6P standard calibration curve.

N-linked glycans were released from EW-NaGlu using PNGase-F at 38° C. for three hours and then labeled with the Fluorophore 8-aminopyrene-1,3,6-Trisulfonate (APTS) at room temperature overnight. Labeled glycans and maltodextrin ladder were analyzed by capillary electrophoresis coupled to LED induced fluorescence detector. Separation was performed using polymeric gel buffer in a coated capillary under −30 kV. Glycan structure assignment was based on the relative migration time and relative percentages of labeled glycans were calculated based on peak areas.

Results: rhNaGlu Blood Brain Barrier Cell Culture Transport

Figure 4A:
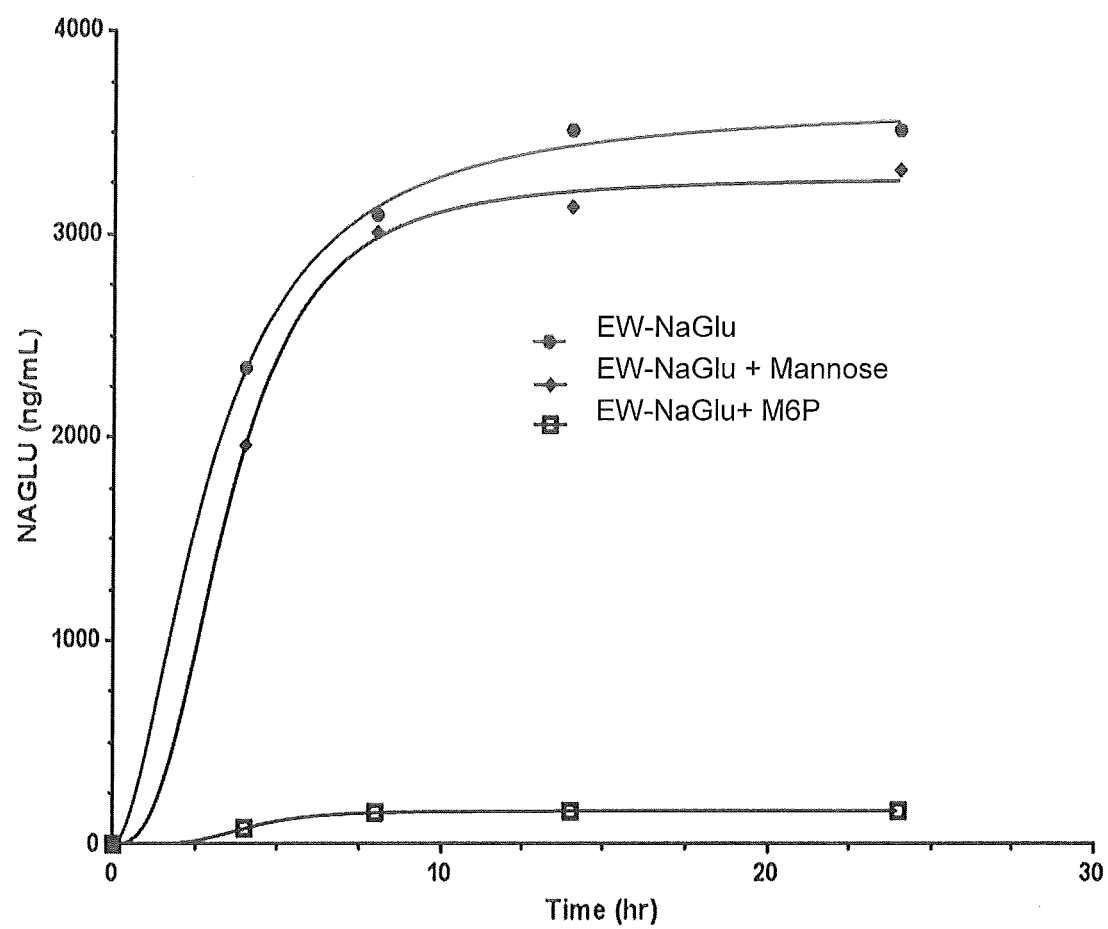
FIG. 4A shows that eggwhite-derived rhNaGlu (EW-NaGlu) is transported across the rat in vitro Blood Brain Barrier assay in a time dependent manner. EW-NaGlu efficiently crosses the endothelial/pericytes cell barrier (●) while Mannose-6-Phosphate blocks eggwhite-derived rhNaGlu uptake (□) but mannose does not (♦).
Figure 4B:
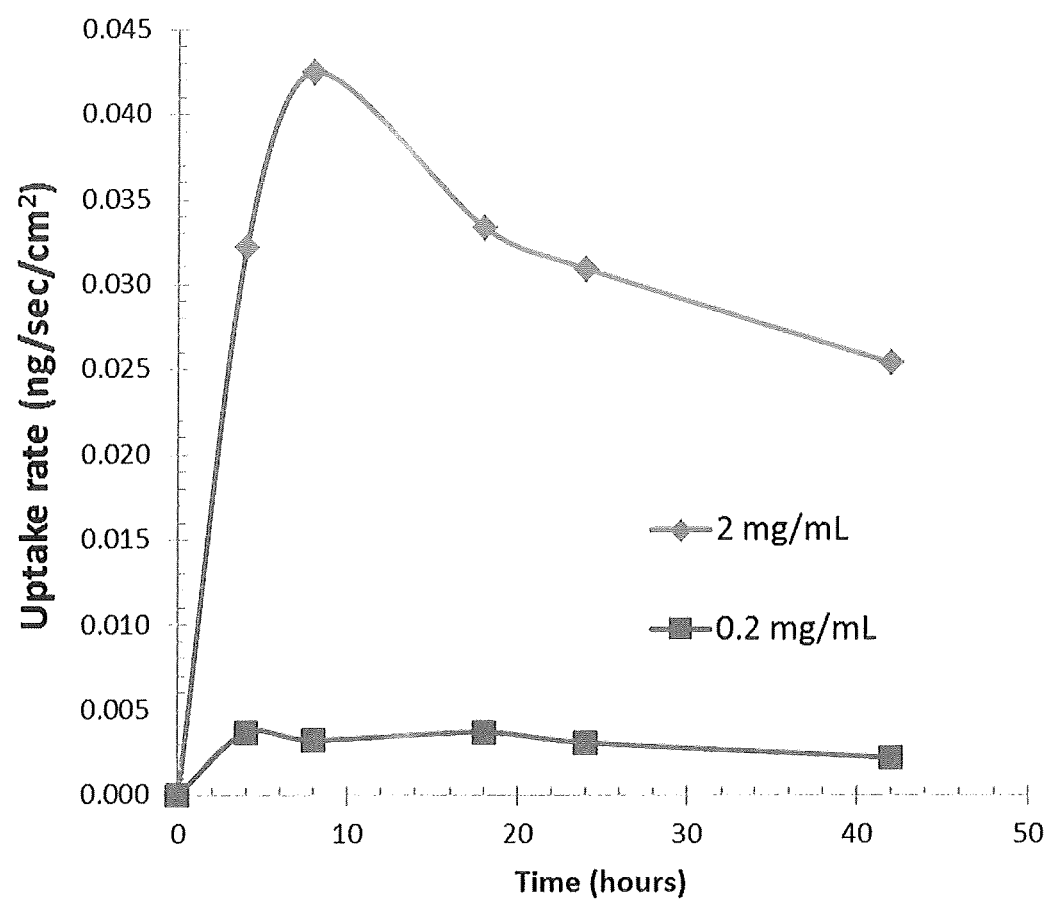
FIG. 4B depicts eggwhite-derived rhNaGlu (EW-NaGlu) is transported across the rat in vitro Blood Brain Barrier assay in a time dependent manner. The maximum eggwhite-derived rhNaGlu uptake rate (~42 ng/sec/cm$^2$) occurs at 8 hours (♦) following the addition of 2 mg/mL to the BBB assay well while a 0.2 mg/mL EW-NaGlu concentration demonstrated a 10-fold less (■) uptake rate (~4 ng/sec/cm$^2$).
Figure 5A:
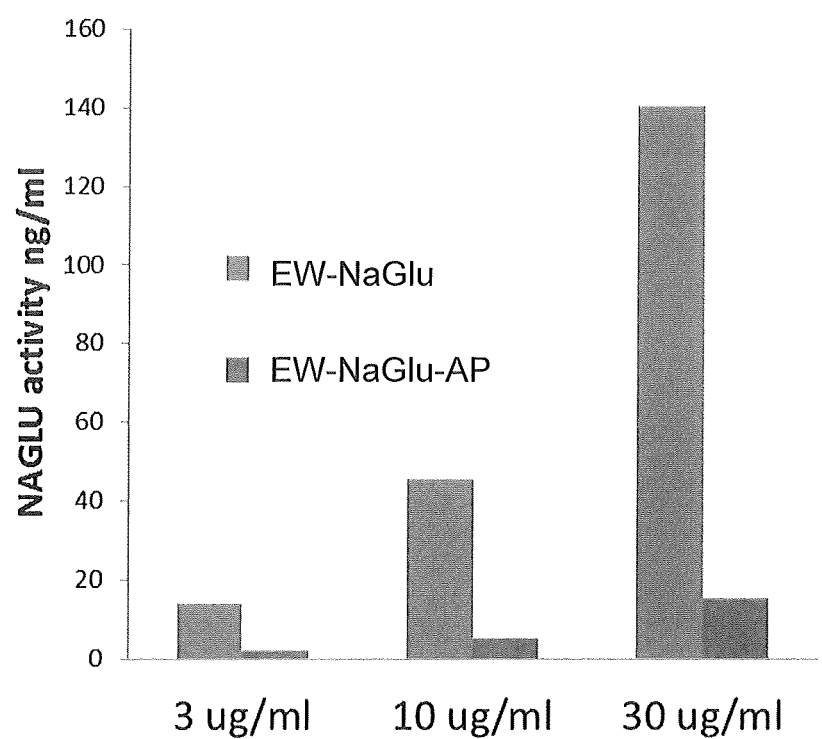
FIG. 5A shows the uptake of EW-NaGlu into NaGlu deficient fibroblasts (GM00156) in M6P dependent manner. Treatment of EW-NaGlu with Alkaline Phosphatase (AP) prevents uptake into human NaGlu deficient fibroblast.
Figure 5B:
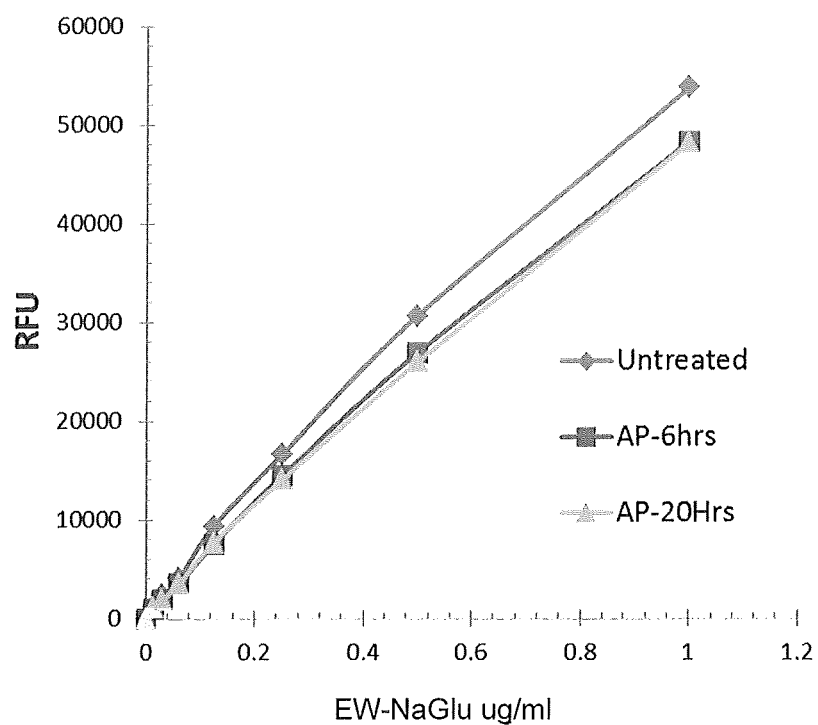
FIG. 5B depicts AP of EW-NaGlu treatment had minimal effect on NaGlu activity.

Recombinant human NaGlu (rhNaGlu) expressed in an egg white (EW) system platform was compared to CHO-derived NaGlu (CHO-NaGlu) purchased from R&D Systems in a Blood Brain Barrier cell culture assay that monitors the ability of NaGlu to be transported across the cell bi-layer (see Materials and Methods Above). On day 4 or 5 following the start of the BBB assay, rhNaGlu was added to the apical side medium at 0.2 mg/mL with or without the addition of 3.3 mM mannose or 3.3 mM mannose-6-phosphate (M6P) (FIG. 4A). As a comparative control, CHO-NaGlu was added at 0.1 mg/mL in a separate well. Enzyme activities for each condition were monitored in the basolateral medium starting at time 0 and again at 4, 8, 14, and 24 hours. rhNaGlu was detected in the basolateral medium starting at 4 hours (2300 ng/mL) and continued rise to 3500 ng/mL by 14 hours where it reached a plateau as indicated by a similar basolateral medium concentration at 24 hours. This is suggestive that equilibrium was reached between transport to the basolateral side and back to the apical side. The addition of 3.3 mM mannose had no impact on rhNaGlu transport whereas the addition of 3.3 mM M6P markedly reduced rhNaGlu transport by <90% suggesting transport is M6P receptor mediated and not influenced by the mannose receptor. From these data, the uptake rate was determined to be ~42 pg/sec/cm² when 2 mg/mL of rhNaGlu was added to the apical side media and ~4 pg/sec/cm² when 0.2 mg/mL was added (FIG. 4B). These combined data demonstrated that rhNaGlu was efficiently transported across the in vitro BBB in a M6P dependent manner with little if any requirement for mannose receptor binding. To further explore the M6P requirement for cell uptake, rhNaGlu was treated with alkaline phosphatase (AP) for 6 hours prior to addition to a NaGlu deficient human fibroblast line. AP treatment blocked rhNaGlu uptake (FIG. 5A) but had no effect on NaGlu enzyme activity (FIG. 5B) demonstrating an M6P requirement for rhNaGlu uptake into fibroblasts.

Figure 6A:
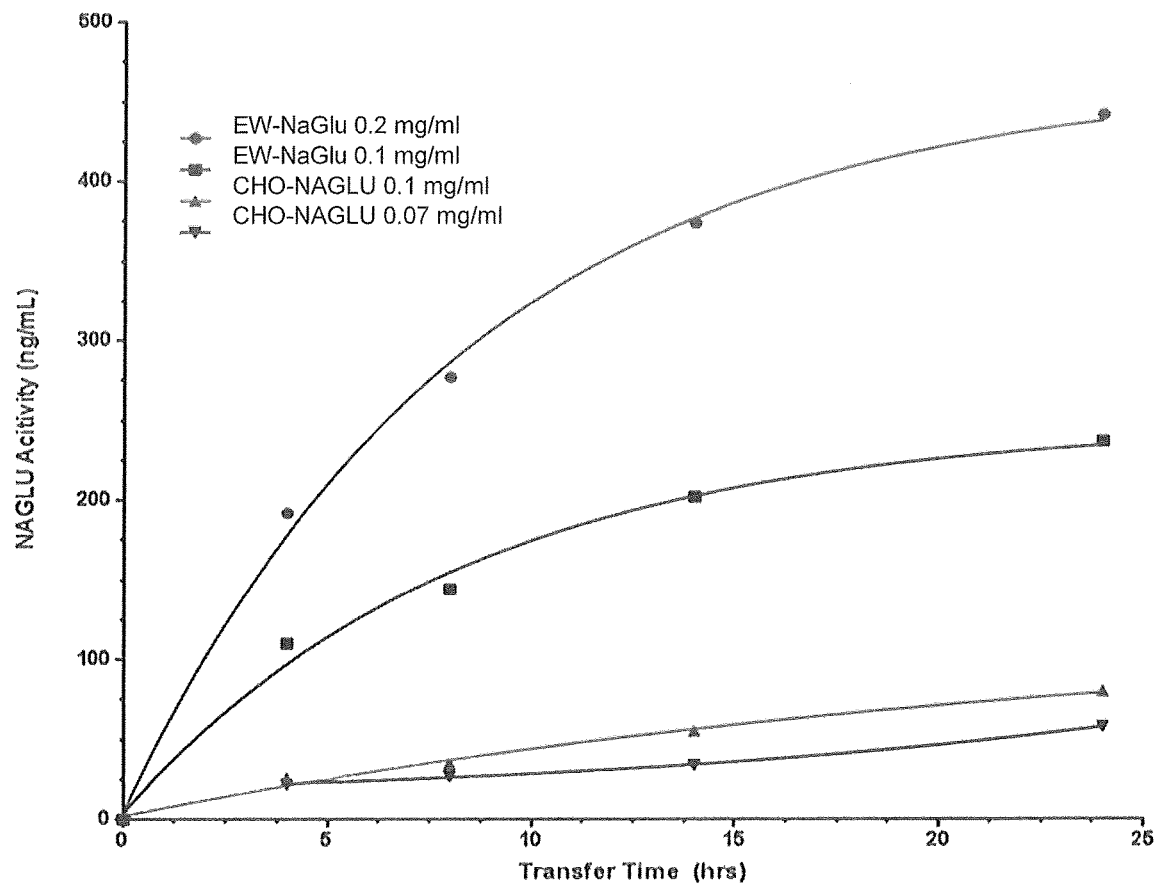
FIG. 6A depicts that EW-NaGlu transport in the BBB cell culture assay is more efficient than the CHO-derived enzyme as shown in a time course transport comparison between 0.2 mg/mL (♦) and 0.1 mg/mL (■) EW-NaGlu to 0.1 mg/mL (▲) and 0.08 mg/mL (▼) CHO-NaGlu.
Figure 6B:
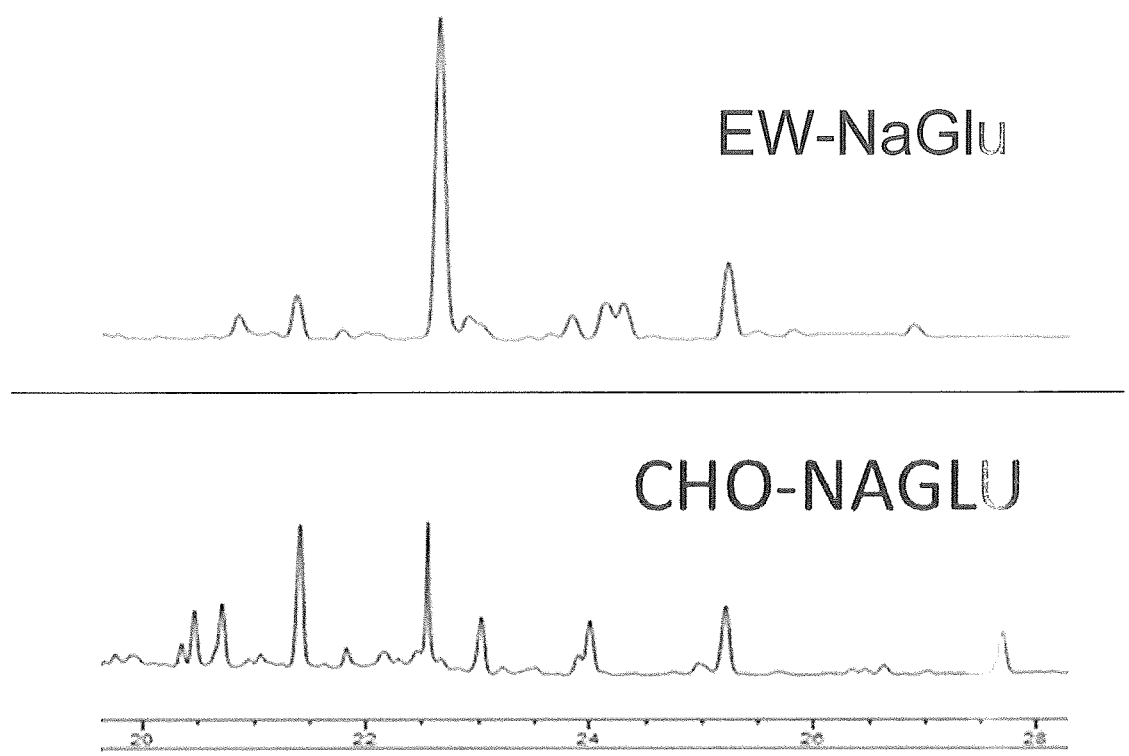
FIG. 6B depicts a CE-LIF N-linked oligosaccharide profiles from EW-NaGlu and CHO-NaGlu.

CHO-NaGlu achieved a plateau concentration of 80 ng/mL (FIG. 6A) in the BBB cell culture assay, which is ~3-fold less than the uptake achieved by EW-NaGlu (240 ng/mL) when similar amounts of enzyme are added to the assay (0.1 mg/mL). Given the impact of M6P on EW-NaGlu transport, the decreased CHO NaGlu transport suggests that CHO produced NaGlu could contain less M6P compared to EW-NaGlu. Previously published work from other groups on CHO NaGlu uptake into MPS-IIIB fibroblasts cells suggested that M6P levels on CHO expressed NaGlu are extremely low or none existent (Weber et al., supra). N-linked oligosaccharide analysis of EW-NaGlu and CHO-NaGlu by CE-LIF demonstrate significant differences in their respective profiles (FIG. 6B).

Figure 7A:
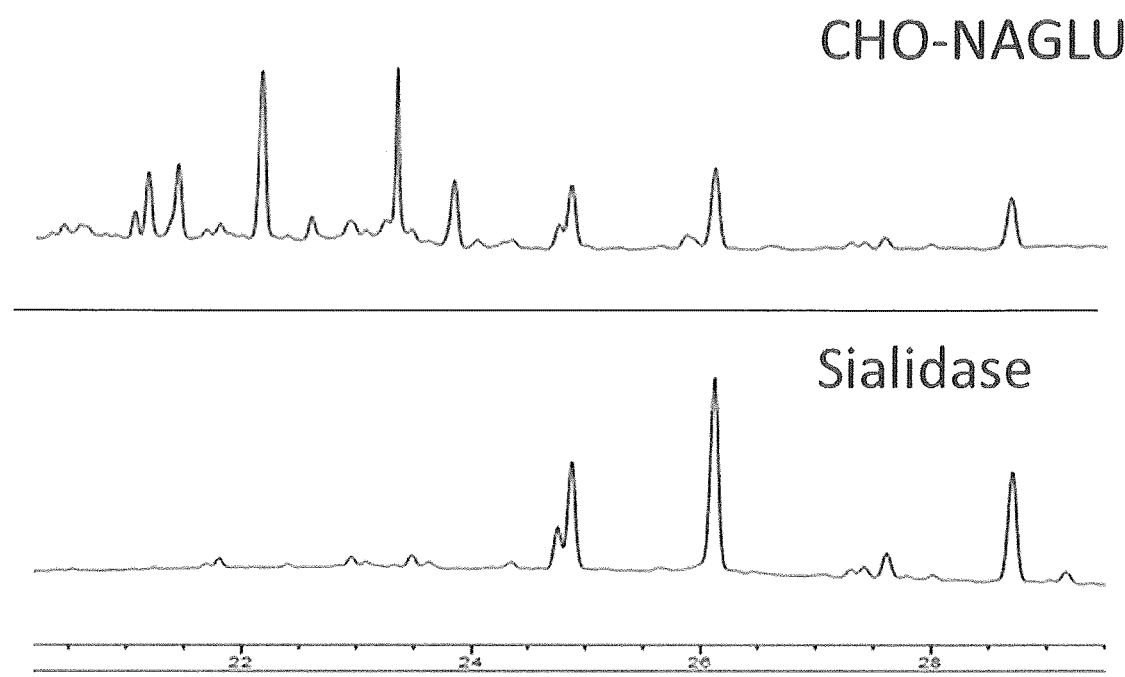
FIG. 7A depicts a CE-LIF N-linked oligosaccharide profiles of CHO-NaGlu and CHO-NaGlu treated with sialidase.
Figure 7B:
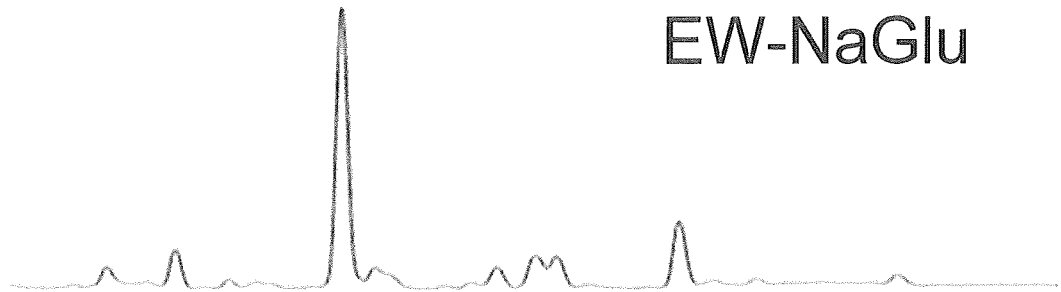
FIG. 7B depicts a CE-LIF N-linked oligosaccharide profiles of EW-NaGlu and EW-NaGlu treated with sialidase.
Figure 7B:
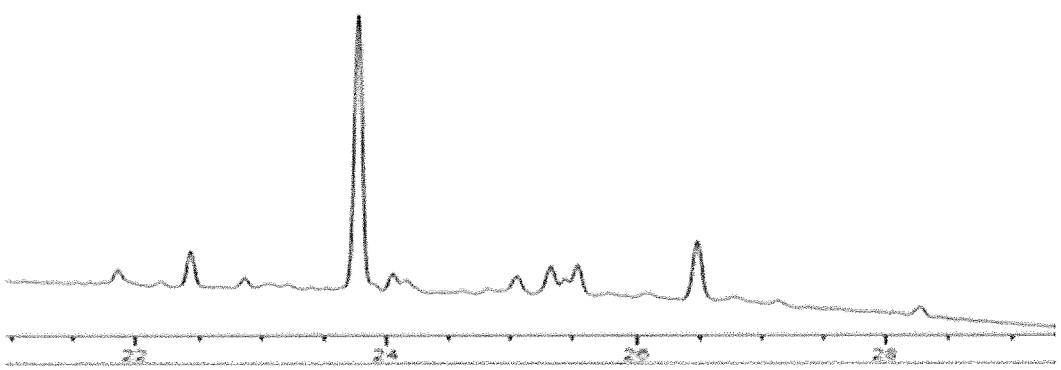

To better understand the observed N-linked oligosaccharide differences between CHO-derived NaGlu and EW-NaGlu, both enzymes were subjected to Sialidase treatment to remove any sialic acid moieties, if any, followed by CE-LIF to resolve the N-linked oligosaccharides (FIGS. 7A and 7B). The untreated CHO-derived NaGlu profile differed significantly from the sialidase-treated sample (FIG. 7A) suggesting a significant amount of the CHO NaGlu carbohydrates are capped with sialic acid, whereas the untreated EW-NaGlu profile looked indistinguishable from the sialidase-treated sample (FIG. 7B). The lack of sialic acid together with the presence of M6P-containing glycans suggest the EW-NaGlu carbohydrate profile is ideal to promote M6P receptor binding with no sialic acid-induced repulsion to prevent receptor binding.

Example 5

Figure 8:
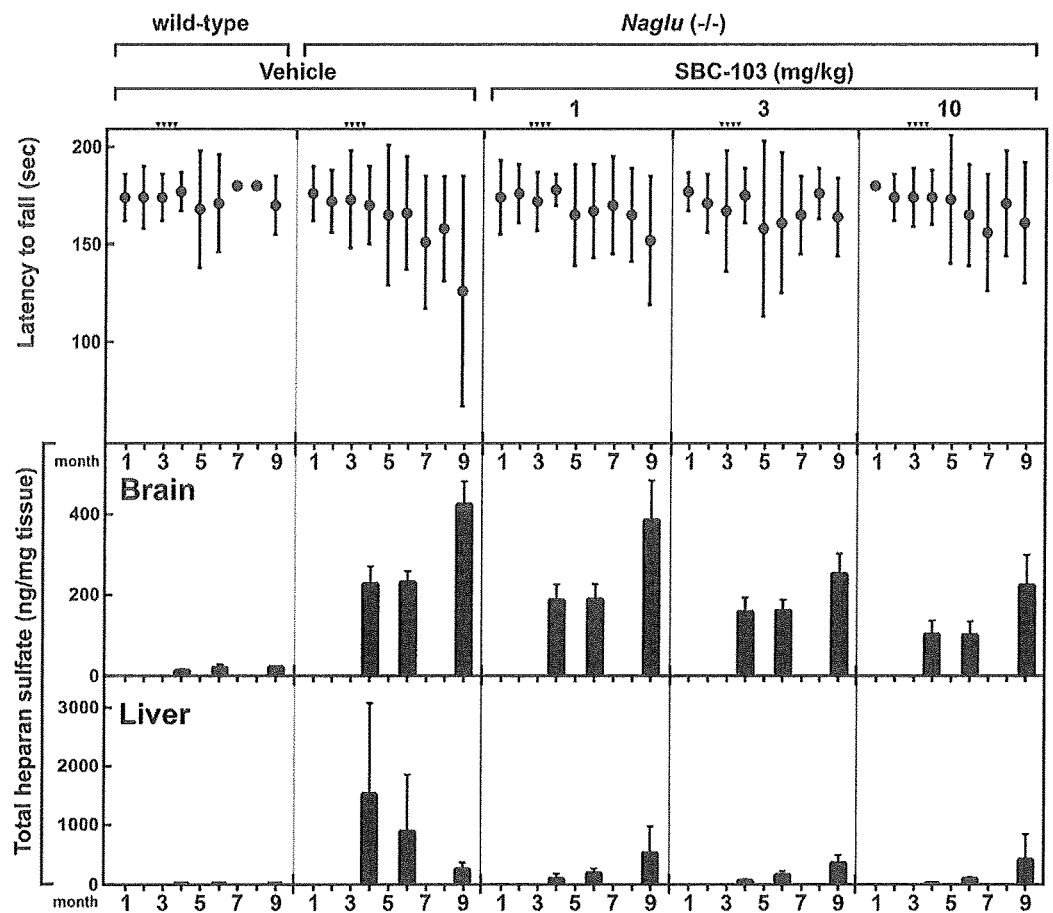
FIG. 8 depicts an assessment of the long-term effects of repeated intravenous administration (4-weeks, once per week) of rhNaGlu in the Naglu-deficient mouse model.

A twelve month intravenous dosing study was performed to determine the efficacy of rhNaGlu in the Naglu-deficient mouse model (FIG. 8). Efficacy was scored on the reduction of heparan sulfate tissue levels and the maintenance of motor skills. Animals around three months of age, including wild-type controls, were intravenously dosed weekly for a total of four weeks (FIG. 8, small arrowheads above graph). The top panel of FIG. 8 shows the RotaRod behavioral test using a rocking paradigm that is scored based on latency to fall over a 180 second time frame. Vehicle-treated Naglu-deficient mice begin to show a decline in motor skills (earlier time to fall) around six months and worsens up to nine months. With increasing doses of rhNaGlu, there is improvement in motor skills in treated knockout animals as compared to vehicle treated animals. Following the 4-week treatment with rhNaGlu the maintenance of motor skills was maintained up to at least 4 months, even to 5 to 6 months.

The lower panels of FIG. 8 indicate the total level of heparan sulfate in brain and liver in nanograms per milligram of tissue. These data show that there is a dose-dependent decrease in both brain and liver heparan sulfate levels. The reduction in tissue heparan sulfate levels appears to correlate with improved motor skill function. Following the 4-week treatment with rhNaGlu, the reduced heparan sulfate levels were maintained up to at least 4 months, even to 5 to 6 months. Although run for twelve months, the twelve month time point was not analyzed due to significant health issues observed in all groups. Some gender differences were also observed in the vehicle knockout animals from four to six months where male mice showed a much larger increase in heparan sulfate levels in the liver as compared to female mice.

Example 6

Figure 9:
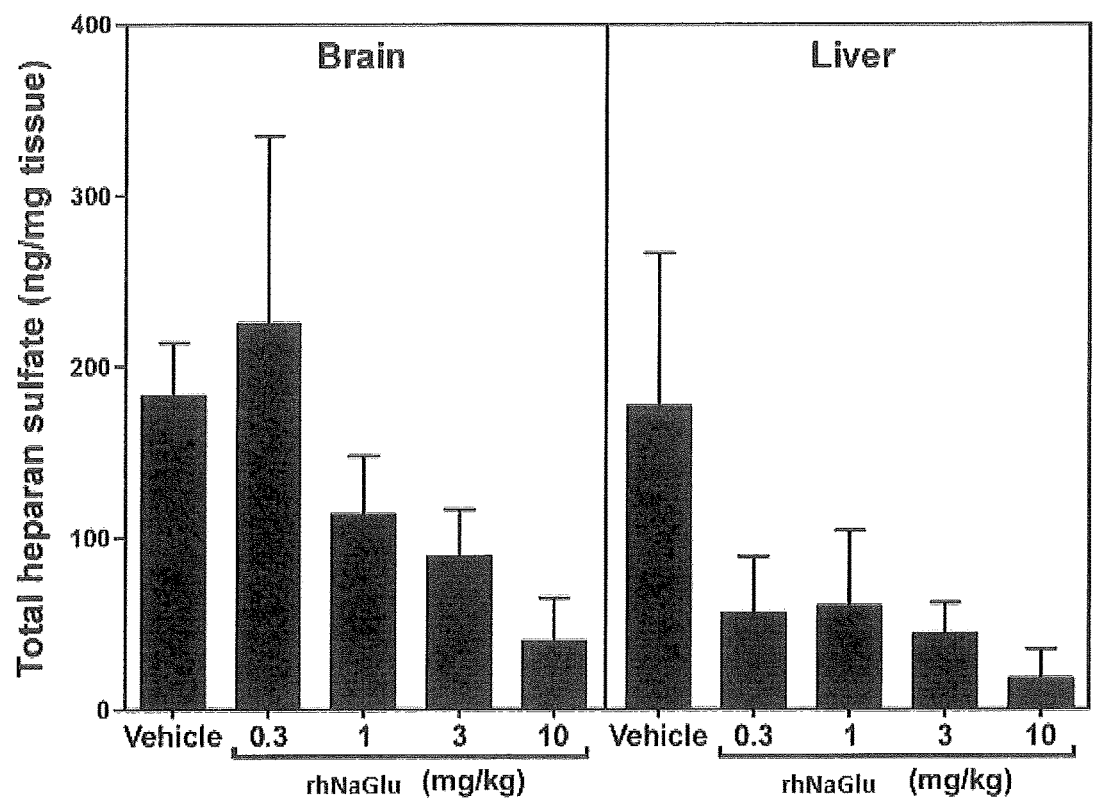
FIG. 9 shows a biweekly IV bolus pharmacodynamic study in Naglu-deficient mice with rhNaGlu.

The goal of this study was to determine if there is a dose dependent reduction in heparan sulfate in the brain and liver tissues after rhNaGlu treatment. In this study 3-6 month old Naglu-deficient mice were dosed intravenously once every two weeks for a total treatment window of eight weeks at a dose of 0.3, 1, 3 and 10 mg/kg (FIG. 9). Four male and four female mice were included per treatment group. Brain and liver samples were harvested and analyzed for heparan sulfate levels the day after the last dose. Total heparan sulfate levels are shown as nanogram per milligram of tissue. These data show there is a dose-dependent heparan sulfate reduction in the brain and liver with increasing doses of rhNaGlu.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human patient with mucopolysaccharidosis (MPSIIIB);
   the method comprising administering intravenously to said patient a therapeutically effective amount of recombinant human N-acetyl-alpha-D-glucosaminidase (rhNaGlu);
   wherein the rhNaGlu comprises mannose-6-phosphate (M6P) and bisecting GlcNAc;
   wherein said patient has previously undergone long-term enzyme replacement with N-acetyl-alpha-D-glucosaminidase and has heparan sulfate (HS) levels in the cerebrospinal fluid (CSF) that are at least 50% reduced from pretreatment levels;
   wherein said patient has an intact blood brain barrier (BBB);
   and
   wherein the therapeutically effective amount of rhNaGlu prevents reaccumulation of HS levels in the CSF.

2. The method of claim 1, wherein said patient is at the age of about 7 or younger and has at least one of a CSF/serum albumin Index of less than about 5, and a CSF/IgG Index of less than about 0.7.

3. The method of claim 1, further comprising measuring one or more of the BBB transfer coefficient ($K^{trans}$), a CSF/serum albumin Index, a CSF/serum IgG Index, and/or a CSF IgG Index in the patient, and selecting the patient based on the presence of a $K^{trans}$ no more than about 125% of a reference $K^{trans}$ that represents an intact BBB in a normal healthy subject, a CSF/serum albumin Index below about 15, and/or a CSF/serum IgG Index less than about 10, and/or a CSF IgG Index less than about 0.85.

4. The method of claim 1, wherein the treatment reduces at least 20% of HS accumulation level in the CSF relative to the level observed prior to the treatment.

5. The method of claim 1, wherein the rhNaGlu is administered at a dose between about 1 mg/kg and about 10 mg/kg to the human patient.

6. The method of claim 1, wherein the intact BBB in said patient comprises:
   a CSF/serum albumin Index below 15;
   a CSF/serum IgG Index less than 10;
   a CSF IgG Index of less than 0.9; and/or
   a $K^{trans}$ no more than 125% of a reference $K^{trans}$ that represents an intact BBB in a normal healthy subject.

7. The method of claim 1, wherein mucopolysaccharidosis IIIB (MPSIIIB) has neurological symptoms, and wherein the symptoms are ameliorated.

8. The method of claim 7, wherein the neurological symptoms of mucopolysaccharidosis IIIB in the human patient is delayed development of speech, progressive mental retardation, neurological dysfunction, delayed neurocognitive and development function or dementia.

9. The method of claim 8, wherein the delayed neurocognitive and development function is measured by the patient's scores on one or more tests selected from the group consisting of Vineland-II, the Bayley Scales of Infant and Toddler Development and Kaufman Assessment Battery for Children.

10. The method of claim 8, wherein the neurological symptoms of mucopolysaccharidosis IIIB in the human patient is measured by assessment of caregiver quality of life, assessment of language, or neurocognitive and developmental function.

* * * * *